(12) United States Patent
Uemoto et al.

(10) Patent No.: US 10,088,401 B2
(45) Date of Patent: Oct. 2, 2018

(54) AUTOMATIC SAMPLE PREPARATION APPARATUS

(71) Applicant: Hitachi High-Tech Science Corporation, Tokyo (JP)

(72) Inventors: Atsushi Uemoto, Tokyo (JP); Tatsuya Asahata, Tokyo (JP); Makoto Sato, Tokyo (JP); Yo Yamamoto, Tokyo (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 0 days.

(21) Appl. No.: 15/317,030

(22) PCT Filed: Jun. 29, 2015

(86) PCT No.: PCT/JP2015/068688
§ 371 (c)(1),
(2) Date: Dec. 7, 2016

(87) PCT Pub. No.: WO2016/002719
PCT Pub. Date: Jan. 7, 2016

(65) Prior Publication Data
US 2017/0122852 A1    May 4, 2017

(30) Foreign Application Priority Data

Jun. 30, 2014   (JP) .................................. 2014-134977

(51) Int. Cl.
*H01J 37/31*      (2006.01)
*G01N 1/44*       (2006.01)
*H01J 37/317*     (2006.01)

(52) U.S. Cl.
CPC ................ *G01N 1/44* (2013.01); *H01J 37/31* (2013.01); *H01J 37/317* (2013.01)

(58) Field of Classification Search
CPC ...... H01J 37/3056; H01J 37/023; H01J 37/18; H01J 37/31; H01J 27/10; G01N 1/286; G01N 1/32; G01N 23/2204; G01N 23/225
(Continued)

(56) References Cited

U.S. PATENT DOCUMENTS 6,039,000 A * 3/2000 Libby ................. H01J 37/3005
118/723 E
6,664,552 B2 * 12/2003 Shichi ................ B23K 15/0006
250/307
(Continued)

FOREIGN PATENT DOCUMENTS

JP     04-076437     3/1992
JP     11-108810     4/1999
(Continued)

OTHER PUBLICATIONS

Japanese Patent Office, Search Report in International Patent Application No. PCT/JP2015/068688 dated Sep. 15, 2015.
(Continued)

*Primary Examiner* — David A Vanore
(74) *Attorney, Agent, or Firm* — Wood Herron & Evans LLP

(57) ABSTRACT

A charged particle beam device (10a) includes a computer (21) which controls multiple charged particle beam irradiation optical systems, the needle (18), and a gas supply portion (17) to transfer a sample piece Q to a predetermined position of the sample piece holder P, based on at least images of a sample piece holder (P), a needle (18), and the sample piece (Q) previously acquired by multiple charged particle beams.

13 Claims, 17 Drawing Sheets

(58) Field of Classification Search
USPC .............. 250/310, 311, 309, 398, 492.1
See application file for complete search history.

(56) References Cited

U.S. PATENT DOCUMENTS

| | | | |
|---|---|---|---|
| 7,700,931 B2* | 4/2010 | Shichi | H01J 37/20 |
| | | | 250/306 |
| 8,247,768 B2* | 8/2012 | Zaykova-Feldman | |
| | | | G01N 23/04 |
| | | | 250/307 |
| 9,275,827 B2* | 3/2016 | Uemoto | H01J 37/20 |
| 9,601,313 B2* | 3/2017 | Brogden | H01J 37/28 |
| 2005/0045821 A1* | 3/2005 | Noji | G01N 23/225 |
| | | | 250/311 |
| 2006/0065854 A1* | 3/2006 | Shichi | H01J 27/10 |
| | | | 250/492.21 |
| 2006/0091325 A1* | 5/2006 | Moore | B82Y 15/00 |
| | | | 250/492.21 |
| 2008/0258056 A1* | 10/2008 | Zaykova-Feldman | |
| | | | G01N 23/04 |
| | | | 250/307 |
| 2013/0248354 A1 | 9/2013 | Keady et al. | |
| 2013/0319849 A1 | 12/2013 | Fuller et al. | |

FOREIGN PATENT DOCUMENTS

| | | |
|---|---|---|
| JP | 11-258130 | 9/1999 |
| JP | 2004-228076 A | 8/2004 |
| JP | 2007-123289 A | 5/2007 |
| JP | 2008-083071 A | 4/2008 |
| JP | 2008-203271 A | 9/2008 |
| JP | 2010-190808 A | 9/2010 |
| JP | 2013-229188 A | 11/2013 |
| WO | 2011148975 A1 | 12/2011 |

OTHER PUBLICATIONS

European Patent Office, Search Report issued in EP 15815501.0 dated Jan. 18, 2018, 10 pages.

* cited by examiner

AUTOMATIC SAMPLE PREPARATION APPARATUS

TECHNICAL FIELD OF THE INVENTION

The present invention relates to an automatic sample preparation apparatus.

RELATED ART

In the related art, an apparatus is known which processes the shape of a sample piece extracted from a sample to a shape suitable for various processes such as observation, analysis, and measurement using an electron beam of a scanning electron microscope, a transmission electron microscope, or the like (for example, refer to Patent Document 1). This apparatus prepares the sample piece by irradiating the sample with a charged particle beam including electrons or ions.

PRIOR ART DOCUMENT

Patent Document

[Patent Document 1] Japanese Unexamined Patent Application, First Publication No. H11-108810

DISCLOSURE OF THE INVENTION

Problems to be Solved by the Invention

In the apparatus of the related art, a technology for improving positional accuracy required so as to accurately process multiple sample pieces into uniform shapes according to miniaturization of the sample pieces, and a technology for appropriately automating a sampling operation of the sample pieces cannot be realized.

In addition, the term "sampling" used in the present specification indicates processing which extracts a sample piece prepared by irradiating the sample with a charged particle beam and processes the sample piece into a shape suitable for various processes such as observation, analysis, and measurement. More specifically, the term "sampling" means transferring a sample piece formed by processing in which a sample is irradiated with a focused ion beam to a sample piece holder.

The present invention is made in consideration of the above-described circumstances, and an object thereof is to provide an automatic sample preparation apparatus in which an operation which extracts a sample piece formed by processing in which a sample is irradiated with an ion beam from a sample and transfers the extracted sample piece to a sample piece holder can be automated.

Means for Solving the Problem

In order to solve the above-described problems and achieve the object, the present invention adopts the following aspects.

(1) According to an aspect of the present invention, there is provided an automatic sample preparation apparatus which automatically prepares a sample piece from a sample, including: a charged particle beam irradiation optical system which performs irradiation with a charged particle beam; a sample stage on which the sample is placed and which moves the sample; a sample piece transfer device for holding and transferring the sample piece separated and extracted from the sample; a sample piece holder-fixing bed which holds a sample piece holder to which the sample piece is transferred; a gas supply portion which irradiates gas forming a deposition film with the charged particle beam; and a computer which controls the charged particle beam irradiation optical system, the sample piece transfer device, and the gas supply portion to transfer the sample piece to the sample piece holder, based on an image which is previously acquired by the charged particle beam with respect to the sample piece held by at least the sample piece transfer device.

(2) In the automatic sample preparation apparatus described in (1), the computer controls a movement of the sample piece transfer device or the sample stage to transfer the sample piece to the sample piece holder, based on positional information which is obtained by template-matching using a template of the sample piece holder by extracting an edge of the sample piece holder from the image acquired by the charged particle beam.

(3) According to another aspect of the present invention, there is provided an automatic sample preparation apparatus which automatically prepares a sample piece from a sample, including at least: a focused ion beam irradiation optical system which performs irradiation with a focused ion beam; a sample stage on which the sample is placed and which moves the sample; a sample piece transfer device for holding and transferring the sample piece separated and extracted from the sample; a sample piece holder-fixing bed which holds a sample piece holder to which the sample piece is transferred; a gas supply portion which irradiates gas forming a deposition film with the focused particle beam; and a computer which controls the focused ion beam irradiation optical system, the sample piece transfer device, and the gas supply portion to transfer the sample piece to the sample piece holder, based on images taken in directions from each other which are previously acquired by the focused ion beam with respect to the sample piece held by at least the sample piece transfer device.

(4) In the automatic sample preparation apparatus described in (3), the computer controls a movement of the sample piece transfer device or the sample stage to transfer the sample piece to the sample piece holder, based on positional information which is obtained by template-matching using a template of the sample piece holder by extracting an edge of the sample piece holder from the image acquired by the focused ion beam.

(5) In the automatic sample preparation apparatus described in (1) or (3), the computer prepares the template of the sample piece held by at least the sample piece transfer device by extracting an edge from the image, and controls a movement of the sample piece transfer device or the sample stage to transfer the sample piece to the sample piece holder based on positional information acquired by template-matching using the template.

(6) In the automatic sample preparation apparatus described in any one of (1) to (5), the computer acquires the image in a state where a structure does not exist on a background of the sample piece held by at least the sample piece transfer device.

(7) In the automatic sample preparation apparatus according to (6), when the computer instructs the movement of the sample piece transfer device or the sample stage to be the state where a structure does not exist on the background of the sample piece held by at least the sample piece transfer device, in a case of not being the state where a structure does not actually exist on the background, the computer moves the sample piece connected to at least the sample piece transfer device to an initial position.

(8) In the automatic sample preparation apparatus described in any one of (1) to (5), the computer acquires the image in a state where the sample piece transfer device rotates such that the sample piece has a predetermined posture.

(9) In the automatic sample preparation apparatus according to (5), the computer acquires the image again in a case where an edge cannot be extracted from the image with respect to a predetermined region of the sample piece held by at least the sample piece transfer device.

(10) In the automatic sample preparation apparatus described in any one of (1) to (9), the computer acquires a distance between the sample piece held by the sample piece transfer device and the sample piece holder based on the image, and the computer controls the movement of the sample piece transfer device or the sample stage to transfer the sample piece to a predetermined position of the sample piece holder based on the distance.

(11) In the automatic sample preparation apparatus according to any one of (1) to (10), the computer finally transfers the sample piece to a predetermined position of the sample piece holder by only a movement in a plane parallel to the sample stage.

(12) In the automatic sample preparation apparatus described in (5), the computer performs shape processing on the sample piece held by the sample piece transfer device before the template is prepared.

(13) In the automatic sample preparation apparatus according to (12), the computer sets the position of the shape processing according to a distance from the sample piece transfer device.

(14) In the automatic sample preparation apparatus described in any one of (1) to (5), the computer performs eccentricity correction when the sample piece transfer device holding the sample piece rotates to have a predetermined posture.

Effects of the Invention

According to the automatic sample preparation apparatus of the present invention, it is possible to automate the operation of extracting the sample piece formed by processing the sample using an ion beam and transferring the sample piece to the sample piece holder. It is possible to accurately transfer the sample piece to the predetermined position of the sample piece holder based on images which are previously acquired of at least the sample piece holder, the sample piece transfer device, and the sample piece.

EMBODIMENTS OF THE INVENTION

Hereinafter, an automatic sample preparation apparatus according to an embodiment of the present invention automatically capable of preparing a sample will be described with reference to the accompanying drawings.

Figure 1:
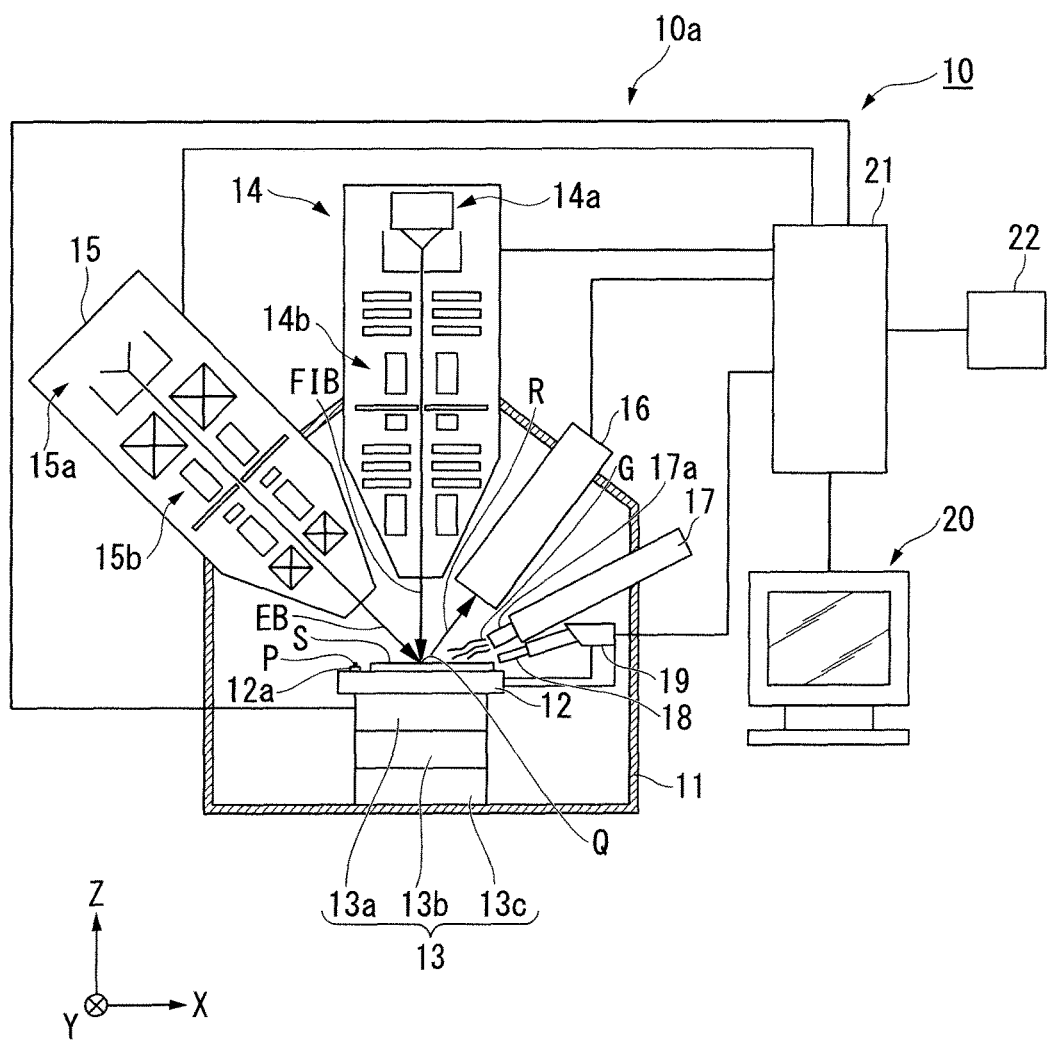
FIG. 1 is a configuration view of an automatic sample preparation apparatus according to an embodiment of the present invention.

FIG. 1 is a configuration view of an automatic sample preparation apparatus 10 including a charged particle beam device 10a according to the embodiment of the present invention. The automatic sample preparation apparatus 10 according to the embodiment of the present invention includes the charged particle beam device 10a. As shown in FIG. 1, the charged particle beam device 10a includes a sample chamber 11 capable of maintaining the internal to the vacuum state, a stage 12 which can fix a sample S and a sample piece holder P inside the sample chamber 11, and a drive mechanism 13 which drives the stage 12. The charged particle beam device 10a includes a focused ion irradiation optical system 14 which irradiates an irradiation object inside a predetermined irradiation region (that is, a scanning range) in the sample chamber 11 with a focused ion beam (FIB). The charged particle beam device 10a includes an electron beam irradiation optical system 15 which irradiates the irradiation object inside a predetermined irradiation region in the sample chamber 11 with an electron beam (EB). The charged particle beam device 10a includes a detector 16 which detects secondary charged particles (secondary electrons, secondary ions, or the like) R which are generated from the irradiation object by the irradiation of the charged particle beam (that is, focused ion beam or electron beam). The charged particle beam device 10a includes a gas supply portion 17 which supplies gas G to the surface of the irradiation object. The charged particle beam device 10a includes a needle 18 which extracts the sample piece Q from the sample S which is fixed to the stage 12, holds the sample piece Q, and installs the sample piece Q to a sample piece holder P, and a needle drive mechanism 19 which drives the needle 18 to transport the sample piece Q. The combination of the needle 18 and the needle drive mechanism 19 is sometimes referred to as a sample piece transfer device. The charged particle beam device 10a includes a display device 20 which displays image data or the like based on secondary charged particles R detected by the detector 16, a computer 21, and an input device 22.

In addition, irradiation objects of the focused ion beam irradiation optical system 14 and the electron beam irradiation optical system 15 are the sample S fixed to the stage 12, the sample piece Q, and the needle 18 which exists in an irradiation region, or the like.

The charged particle beam device 10a according to the present embodiment can realize various processing by sputtering (etching processing or the like) and formation of a deposition film by irradiating the surface of the irradiation object with a focused ion beam while scanning the surface with the focused ion beam. The charged particle beam device 10a can realize processing in which sample piece Q for a transmission observation by a transmission electron microscope (for example, a thin sample, a needle-shaped sample, or the like) is formed from the sample S. The charged particle beam device 10a can realize processing in which the sample piece Q installed on the sample piece holder P is formed in a thin film having a desired thickness (for example, 10 to 20 nm or the like) suitable for the transmission observation by the transmission electron microscope. The charged particle beam device 10a can realize observation with respect to the surface of the irradiation object by irradiating the surface of the irradiation object such as the sample piece Q and the needle 18 with a focused ion beam or an electron beam while scanning the surface of the irradiation object with the focused ion beam or the electron beam.

Figure 2:
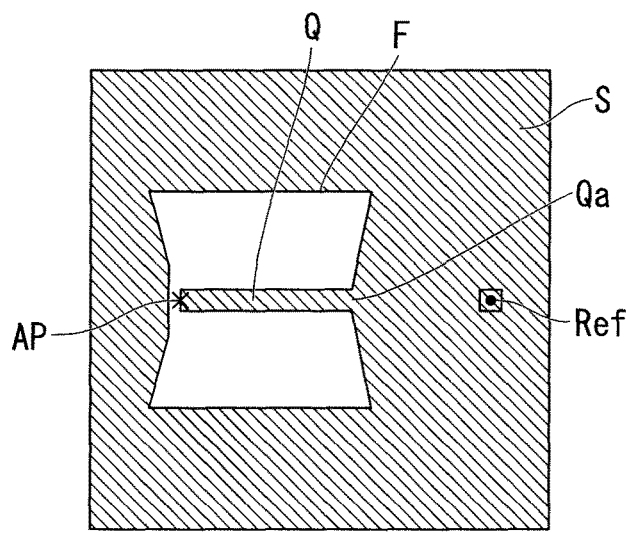
FIG. 2 is a plan view showing a sample piece which is formed on a sample of the automatic sample preparation apparatus according to the embodiment of the present invention.

FIG. 2 is a plan view showing the sample piece Q which is formed on the sample S of the charged particle beam device 10a according to the embodiment of the present invention. The sample piece Q of the sample S is etched such that a support portion Qa connected to the sample S remains and the peripheral portions of the side portion side and the bottom portion side are cut and removed. The sample piece Q is supported to the sample S in a cantilever manner by the support portion Qa.

The sample chamber 11 can be exhausted until the inside of the sample chamber 11 becomes a desired vacuum state by an exhaust device (not shown), and is configured such that the desired vacuum state can be maintained.

Figure 3:
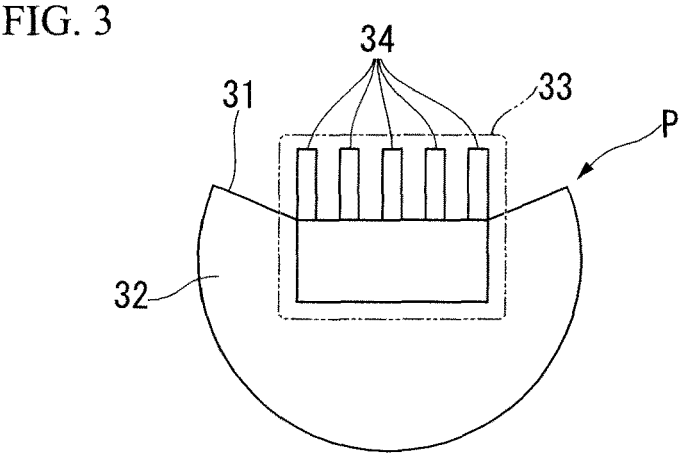
FIG. 3 is a plan view showing a sample piece holder of the automatic sample preparation apparatus according to the embodiment of the present invention.
Figure 4:
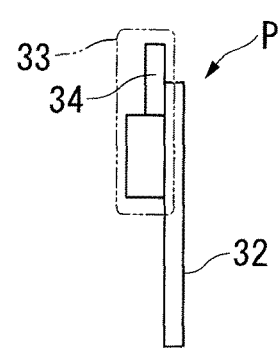
FIG. 4 is a side view showing the sample piece holder of the automatic sample preparation apparatus according to the embodiment of the present invention.

The stage 12 holds the sample S. The stage 12 includes a holder-fixing bed 12a which holds the sample piece holder P. FIG. 3 is a plan view of the sample piece holder P, and FIG. 4 is a side view thereof. The sample piece holder P includes a semicircular plate-shaped base portion 32 having a notch 31, and a sample bed 33 which is fixed to the notch 31. For example, the base portion 32 is formed of metal and is formed in a circular plate shape having a diameter of 3 mm and a thickness of 50 μm. For example, the sample bed 33 is formed from a silicon wafer by a MEMS process and is bonded to the notch 31 by a conductive adhesive. The sample bed 33 includes multiple (for example, five or the like) columnar portions (pillars) 34 which are formed in a comb tooth shape, are disposed to protrude so as to be separated from each other, and have widths different from each other. The widths of respective columnar portions 34 different from each other and the transferred sample piece Q associated with each columnar portion 34 are stored in the computer 21, and it is possible to recognize the sample pieces Q held by the multiple columnar portions 34 without making a mistake. In each columnar portion 34, for example the thickness of the tip portion is formed to be 10 μm or less, and each columnar portion 34 holds the sample piece Q attached to the tip surface of the columnar portion 34.

The drive mechanism 13 is accommodated inside the sample chamber 11 in a state where the drive mechanism 13 is connected to the stage 12, and displaces the stage 12 with respect to a predetermined axis according to a control signal output from the computer 21. The drive mechanism 13 includes a movement mechanism 13a which moves the stage 12 to be parallel along an X axis and a Y axis which are parallel to a horizontal surface and orthogonal to each other, and a Z axis which is a vertical direction orthogonal to the X axis and the Y axis. The drive mechanism 13 includes a tilt mechanism 13b which rotates the stage 12 around the X axis and the Y axis, and a rotation mechanism 13c which rotates the stage 12 around the Z axis.

The focused ion beam irradiation optical system 14 is fixed to the sample chamber 11 in a state where a beam-emitting portion (not shown) inside the sample chamber 11 faces the stage 12 at a position above the stage 12 in the vertical direction in the irradiation region, and an optical axis is parallel to the vertical direction. Accordingly, the irradiation object such as the sample S fixed to the stage 12, the sample piece Q, and the needle 18 existing in the irradiation region can be irradiated with a focused ion beam which is directed from the upper portion in the vertical direction to the lower portion in the vertical direction.

The focused ion beam irradiation optical system 14 includes an ion source 14a which generates ions, and an ion optical system 14b which focuses and deflects the ions emitted from the ion source 14a. The ion source 14a and the ion optical system 14b are controlled by a control signal output from the computer 21, and an irradiation position and irradiation conditions of the focused ion beam, and the like are controlled by the computer 21. For example, the ion source 14a includes a liquid metal ion source which uses liquid gallium or the like, a plasma type ion source, a gas electric field ionization type ion source, or the like. For example, the ion optical system 14b includes a first electrostatic lens such as a condenser lens, an electrostatic deflector, a second electrostatic lens such as an objective lens, or the like.

The electron beam irradiation optical system 15 is fixed to the sample chamber 11 in a state where a beam-emitting portion (not shown) inside the sample chamber 11 faces the stage 12 in an inclination direction which is inclined by a predetermined angle with respect to the vertical direction of the stage 12 in the irradiation region, and an optical axis is parallel to the inclination direction. Accordingly, the irradiation object such as the sample S fixed to the stage 12, the sample piece Q, and the needle 18 existing in the irradiation region can be irradiated with an electron beam which is directed from the upper portion in the inclination direction to the lower portion in the inclination direction.

The electron beam irradiation optical system 15 includes an electron source 15a which generates electrons, and an electron optical system 15b which focuses and deflects the electrons emitted from the electron source 15a. The electron source 15a and the electron optical system 15b are controlled by a control signal output from the computer 21, and such as an irradiation position and irradiation conditions of the electron beam are controlled by the computer 21. For example, the electron optical system 15b includes an electromagnetic lens, a deflector, or the like.

In addition, the positions of the electron beam irradiation optical system 15 and the focused ion beam irradiation optical system 14 are exchanged, the electron beam irradiation optical system 15 may be disposed in the vertical direction, and the focused ion beam irradiation optical system 14 may be disposed in the inclination direction which is inclined with respect to the vertical direction by a predetermined angle.

The detector 16 detects strength (that is, amounts of secondary charged particles) of secondary charged particles (that is, secondary electrons and secondary ions) R emitted from the irradiation object when the irradiation object such as the sample S and the needle 18 is irradiated with the focused ion beam or electron beam, and outputs information of the detection amounts of the secondary charged particles R. The detector 16 is disposed at a position at which the amounts of the secondary charged particles R can be detected in the sample chamber 11, for example, at a position inside the irradiation region which is inclined to the irradiation object such as the sample S and is positioned above the irradiation object, and the detector 16 is fixed to the sample chamber 11.

A gas injection portion (not shown) of the gas supply portion 17 faces the stage 12 in the sample chamber 11, and the gas supply portion 17 is fixed to the sample chamber 11. The gas supply portion 17 can supply etching gas for selectively promoting etching of the sample S performed by the focused ion beam according to the material of the sample S, deposition gas for forming a deposition film formed by deposits such as metal or an insulating material, or the like to the sample S. For example, the gas supply portion 17 supplies etching gas such as xenon fluoride with respect to a Si-based sample S or water with respect to an organic sample S to the sample S while irradiating the sample S with the focused ion beam, and selectively promotes the etching. In addition, for example, the gas supply portion 17 supplies compound gas containing such as phenantherene, platinum, carbon, or tungsten to the sample S as the deposition gas while irradiating the sample S with the focused ion beam, and deposits solid components decomposed from the deposition gas to the surface of the sample S.

The needle drive mechanism 19 is accommodated inside the sample chamber 11 in a state where the needle 18 is connected to the needle drive mechanism 19, and displaces the needle 18 according to the control signal output from the computer 21. The needle drive mechanism 19 is integrally provided with the stage 12, and for example, if the stage 12 rotates around a tilt axis (that is, X axis or Y axis) by the tilt mechanism 13b, the needle drive mechanism 19 integrally moves with the stage 12. The needle drive mechanism 19 includes a movement mechanism (not shown) which moves the needle 18 to be parallel to each of three-dimensional coordinate axes, and a rotation mechanism (not shown) which rotates the needle 18 around the center axis of the needle 18. Moreover, the three-dimensional coordinate axes are independent from a rectangular triaxial coordinate system of the stage 12 of the sample S. In the rectangular triaxial coordinate system of the stage 12 including a two-dimensional coordinate axes parallel to the surface of the stage 12, in a state where the surface of the stage 12 is inclined or rotated, the coordinate system of the needle 18 is inclined or rotated.

The computer 21 is disposed outside the sample chamber 11, and the display device 20 and the input device 22 such as a mouse or a keyboard which outputs a signal corresponding to the input operation of an operator are connected to the computer 21.

The computer 21 integrally controls the operation of the charged particle beam device 10a by the signal input from the input device 22, a signal generated by preset automatic operation control processing, or the like.

The computer 21 converts the detection amounts of the secondary charged particles R detected by the detector 16 while scanning the irradiation position of the charged particle beam to a luminance signal associated with the irradiation position. The computer 21 generates image data indicating the shape of the irradiation object according to the two-dimensional position distribution of the detection amounts of the secondary charged particles R. In an absorption current image mode, the computer 21 detects an absorption current flowing to the needle 18 while scanning the irradiation position of the charged particle beam, and generates absorption current image data indicating the shape of the needle 18 by the two-dimensional position distribution of the absorption current. The computer 21 displays a screen for performing operations such as enlargement, contraction, movement, or rotation of each image data along with each generated image data on the display device 20. The computer 21 displays a screen for performing various settings such as mode selection and processing set in an automatic sequence control on the display device 20.

The charged particle beam device 10a according to the embodiment of the present invention includes the above-described configuration, and next, the operation of the charged particle beam device 10a will be described.

Hereinafter, an operation of automatic sampling performed by the computer 21, that is, an operation which automatically moves the sample piece Q formed in advance by the processing of the sample S with the charged particle beam (focused ion beam) to the sample piece holder P will be described.

Figure 5:
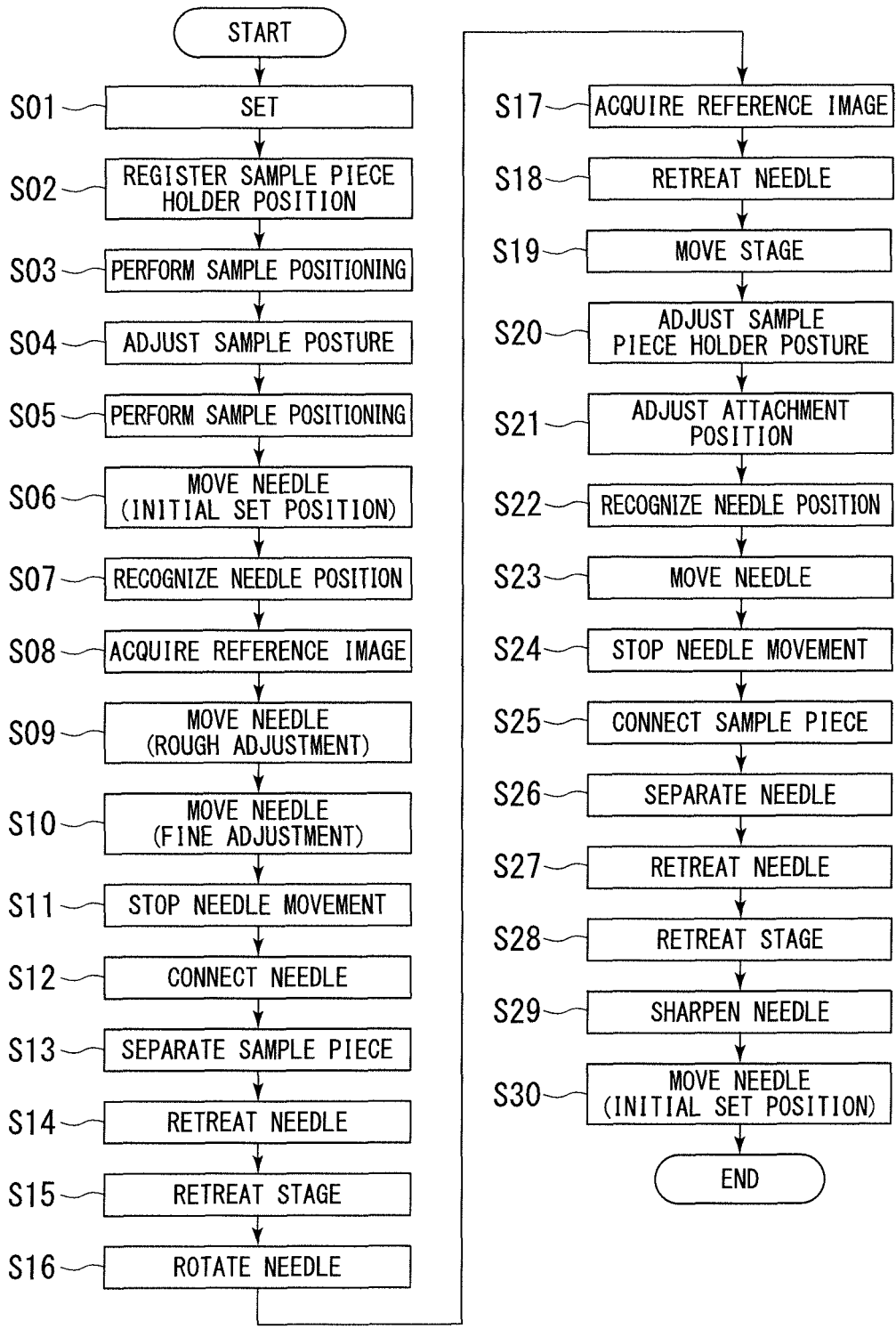
FIG. 5 is a flowchart showing an operation of the automatic sample preparation apparatus according to the embodiment of the present invention.

FIG. 5 is a flowchart showing the operation of the charged particle beam device 10a according to the embodiment of the present invention. First, the computer 21 performs the mode selection such as the presence or absence of a posture control mode described below and the processing setting (setting of a processing position, a dimension, or the like) according to the input of the operator when an automatic sequence starts (Step S01).

(Template Preparation Process of Pillar)

Next, the computer 21 performs a template preparation process of the columnar portion (pillar) 34. The computer 21 prepares the template of the columnar portion (pillar) 34 at the beginning of the sampling process. The computer 21 prepares the template for each columnar portion (pillar) 34. The computer 21 performs coordinate acquisition and template preparation of the columnar portion (pillar) 34 integrally, and performs inspection by determining the shape of the columnar portion (pillar) 34 using template-matching. For example, the computer 21 stores edge information, CAD information, or the like in advance as the template of the columnar portion (pillar) 34 which is used for the template-matching. The computer 21 determines the shape of the columnar portion (pillar) 34 by scores of the template-matching, and for example, in a case where the columnar portion (pillar) 34 does not have a predetermined shape, the computer 21 performs the setting such that the next columnar portion (pillar) 34 is used.

In this template preparation process, first, the computer 21 performs position registration processing of the sample piece holder P installed on the holder-fixing bed 12a of the stage 12 by the operator (Step S02).

In this position registration processing, first, the computer 21 drives the stage 12 by the drive mechanism 13 as the operation of rough adjustment, and positions the irradiation region at the position of the sample piece holder P to which the sample bed 33 is attached. Next, as the operation of fine adjustment, the computer 21 extracts the positions of multiple columnar portions 34 configuring the sample bed 33 using the template prepared from a design shape of the sample bed 33 in advance from each image data generated by the irradiation of the charged particle beam (each of the focused ion beam and the electron beam). In addition, the computer 21 stores (registration-processes) the extracted position coordinate of each columnar portion 34 as an attachment position of the sample piece Q.

The computer 21 sequentially performs the position registration processing by the number of the sample pieces Q in which the automatic sampling is performed. The computer 21 performs the position registration processing of the sample piece holder P before the movement of the sample piece Q described below, and previously confirms that an appropriate sample bed 33 exists in actual.

In addition, in a case where multiple sample piece holders P are installed on the holder-fixing bed 12a, the computer 21 records the position coordinate of each sample piece holder P and the image data of the sample piece holder P along with a code number with respect to each sample piece holder P. In addition, the computer 21 stores (registration-processes) the code number and the image data corresponding to the position coordinate of each columnar portion 34 of each sample piece holder P. Accordingly, in a case where dozens of the sample pieces Q are prepared, the computer 21 can call the specific columnar portion 34 of the specific sample piece holder P to which each sample piece Q is attached in the visual field of the charged particle beam.

In addition, in the position registration processing, if the sample piece holder P itself or the columnar portion 34 is deformed or damaged and the state is not a state where the sample piece Q is attached, the computer 21 registers a corresponding "unusable state" (a state where the sample piece Q is not attached) along with the position coordinate, the image data, and the code number. Accordingly, when the movement of the sample piece Q described below is performed, the "unusable" sample piece holder P or columnar portion 34 is skipped, and the computer 21 can attach the sample piece Q to a normal sample piece holder P or columnar portion 34.

Next, the computer 21 recognizes a reference mark Ref which is formed on the sample S when automatic processing in which the sample piece Q is formed in the sample S in advance is performed, using the image data which is generated by irradiating the sample S with the charged particle beam. The computer 21 stores information of a relative positional relationship between a processing irradiation frame F and the reference mark Ref when the sample piece Q is formed on the sample S by the irradiation of the focused ion beam in advance. The computer 21 recognizes the position of the sample piece Q from the known relative positional relationship between the reference mark Ref and the sample piece Q using the recognized reference mark Ref, and performs the positioning of the sample piece Q (Step S03).

Next, the computer 21 drives the stage 12 by the drive mechanism 13, and rotates the stage 12 around the Z axis by an angle corresponding to the posture control mode such that the posture of the sample piece Q becomes a predetermined posture (for example, a posture or the like suitable for the extraction performed by the needle 18) (Step S04).

Next, the computer 21 recognizes the reference mark Ref using the image data which is generated by irradiating the sample S with the charged particle beam. The computer 21 recognizes the position of the sample piece Q from the known relative positional relationship between the reference mark Ref and the sample piece Q, and performs the positioning of the sample piece Q (Step S05).

Next, the computer 21 moves the needle 18 to an initial set position by the needle drive mechanism 19. For example, the initial set position is a predetermined position or the like inside the visual field region set in advance, and is a predetermined position or the like around the sample piece Q which positioning is completed inside the visual field region. After the computer 21 moves the needle 18 to the initial set position, the computer 21 lowers a nozzle 17a on the tip of the gas supply portion 17 from a standby position above the stage 12 in the vertical direction to a predetermined position around the sample piece Q (Step S06).

When the computer 21 moves the needle 18, the computer 21 can accurately ascertain the position of the sample piece Q using the reference mark Ref which is formed on the sample S when the automatic processing for forming the sample piece Q is performed, and can appropriately move the needle 18 even when the movement is a three-dimensional movement. Since the reference mark Ref is a mark (for example, drift correction mark) which indicates the position reference of processing, even when the shape of the sample piece Q is changed due to processing, the position of the reference mark Ref is not changed. The computer 21 can accurately move the needle 18 using the reference mark Ref with respect to the sample piece Q which is formed with the reference mark Ref as a reference.

Next, the computer 21 performs processing of the following Step S07 to Step S11 as processing in which the computer 21 causes the needle 18 to come into contact with the sample piece Q.

First, the computer 21 switches the mode to the absorption current image mode, and recognizes the position of the needle 18 (Step S07). The computer 21 detects the absorption current which flows to the needle 18 by irradiating the needle 18 with the charged particle beam while scanning the irradiation position, and generates the absorption current image data indicating the two-dimensional position distribution of the absorption current with multiple planes different from each other. The computer 21 acquires the absorption current image data on an XY plane (a plane perpendicular to the optical axis of the focused ion beam) by the irradiation of the focused ion beam, and acquires the image data on an XYZ plane (a plane perpendicular to the optical axis of the electron beam) by the irradiation of the electron beam. The computer 21 detects the position of the tip of the needle 18 in a three-dimensional space using the absorption current image data acquired from two different directions.

In addition, the computer 21 may drive the stage 12 by the drive mechanism 13 using the detected position of the tip of the needle 18, and may set the position of the tip of the needle 18 to the center position (visual field center) of the visual field region which is set in advance.

(Template Preparation Process of Needle)

Figure 6:
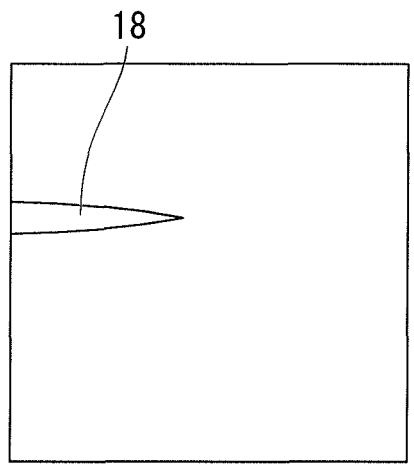
FIG. 6 is a view showing a template of a tip of a needle which is obtained by a focused ion beam of the automatic sample preparation apparatus according to the embodiment of the present invention.
Figure 7:
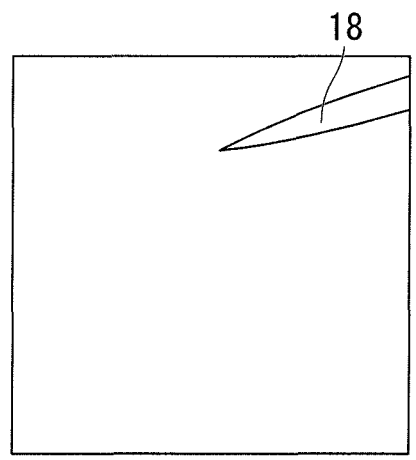
FIG. 7 is a view showing a template of the tip of the needle which is obtained by an electron beam of the automatic sample preparation apparatus according to the embodiment of the present invention.

Next, the computer 21 acquires a template (reference image data) for template-matching with respect to the shape of the tip of the needle 18 using the detected position of the tip of the needle 18 (Step S08). FIG. 6 is a view showing the template of the tip of the needle 18 obtained by the focused ion beam, and FIG. 7 is a view showing the template of the tip of the needle 18 obtained by the electron beam. The computer 21 drives the stage 12 by the drive mechanism 13, and irradiates the needle 18 with the charged particle beam (each of the focused ion beam and the electron beam) while scanning the irradiation position in a state where the sample piece Q is retreated from the visual field region. The computer 21 acquires the image data indicating the position distribution in multiple different planes of the secondary charge particles R emitted from the needle 18 by the irradiation of the charged particle beam. The computer 21 acquires the image data on the XY plane by the irradiation of the focused ion beam, and acquires the image data of the XYZ plane (the plane perpendicular to the optical axis of the electron beam) by the irradiation of the electron beam. The computer 21 acquires the image data by the focused ion beam and the electron beam, and stores the acquired image data as a template (reference image data).

Since the computer 21 has the image data which is actually acquired immediately before moving the needle 18 as rough adjustment and fine adjustment as the reference image data, the computer 21 can perform pattern matching with high accuracy regardless of the shape of the needle 18.

In addition, since the computer 21 acquires the image data in the state where the stage 12 is retreated and a complicated structure does not exist on the background, the computer 21 can acquire the template (reference image data) capable of clearly ascertaining the shape of the needle 18 in a state where influences of the background are excluded.

In addition, when the computer 21 acquires the image data, the computer 21 uses image acquisition conditions such as appropriate magnification, brightness, or contrast stored in advance for increasing recognition accuracy of the object In addition, instead of the computer 21 having the image data of the secondary charged particle R as the reference image, the computer 21 may have the absorption current image data as the reference image. In this case, the computer 21 does not perform retreating of the sample piece Q from the visual field region by driving of the stage 12, and the computer 21 may acquire the absorption current image data with respect to two planes different from each other.

(Sample Piece Pick-Up Process)

Next, the computer 21 performs the needle movement (rough adjustment) in which the needle 18 is moved by the needle drive mechanism 19 (Step S09). The computer 21 recognizes the reference mark Ref (refer to FIG. 2 described above) which is formed on the sample S in advance by the irradiation of the focused ion beam when the sample piece Q is formed, using the image data generated by irradiating the sample S with each of the focused ion beam and the electron beam. The computer 21 sets a movement target position AP of the needle 18 using the recognized reference mark Ref. The computer 21 has the movement target position AP as a position required for performing the processing in which the needle 18 and the sample piece Q are connected by the deposition film, and the movement target position AP is associated with a predetermined positional relationship with respect to the processing irradiation frame F at the time of the formation of the sample piece Q. The computer 21 stores the information of the relative positional relationship between the processing irradiation frame F and the reference mark Ref at the time of forming the sample piece Q on the sample S by the irradiation of the focused ion beam. In addition, the computer 21 may set collectively the reference mark Ref, the processing irradiation frame F, and the movement target position AP related to each other in advance at a time when the sample piece Q is formed or the like, or may set the reference mark Ref, the processing irradiation frame F, and the movement target position AP in appropriate combinations at different timings. The computer 21 sets the reference mark Ref, the processing irradiation frame F, and the movement target position AP, and stores the reference mark Ref, the processing irradiation frame F, and the movement target position AP in a mutually associated manner.

The computer 21 moves the position of the tip of the needle 18 into a three-dimensional space toward the movement target position AP using the recognized reference mark Ref and the relative positional relationship among the reference mark Ref, the processing irradiation frame F, and the movement target position (a predetermined position on the sample piece Q) AP. When the computer 21 moves the needle 18 in a three-dimensional manner, for example, first, the computer 21 moves the needle 18 in the X direction and the Y direction, and thereafter, moves the needle 18 in the Z direction.

When the computer 21 moves the needle 18, the computer 21 can accurately ascertain the position of the sample piece Q using the reference mark Ref and appropriately moves the needle 18 even when the movement is a three-dimensional manner with respect to the movement target position AP. Since the position of the reference mark Ref is not changed even when the shape of the sample piece Q is changed by the processing, the computer 21 can accurately move the needle 18 with respect to the sample piece Q using the movement target position AP associated with the reference mark Ref.

Figure 8:
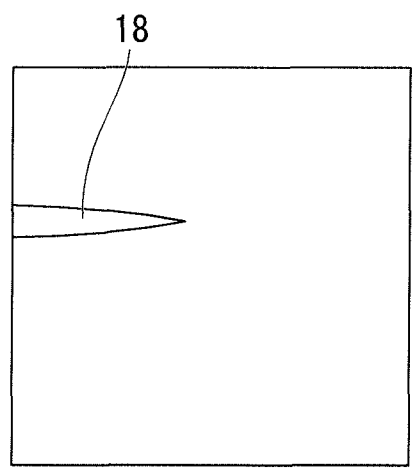
FIG. 8 is a view showing the tip of the needle in image data which is obtained by the focused ion beam of the automatic sample preparation apparatus according to the embodiment of the present invention.
Figure 9:
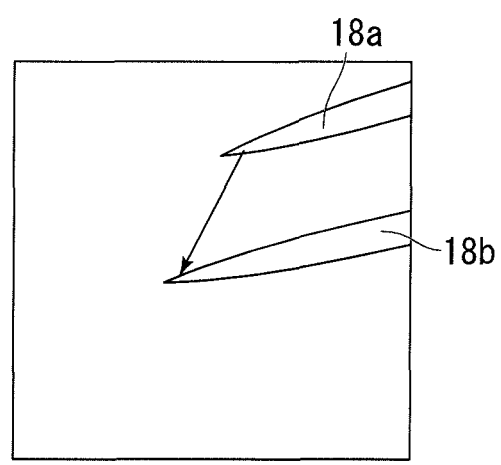
FIG. 9 is a view showing the tip of the needle in the image data which is obtained by the electron beam of the automatic sample preparation apparatus according to the embodiment of the present invention.

FIGS. 8 and 9 show this aspect, particularly, FIG. 8 is a view showing the tip of the needle 18 in image data which is obtained by the focused ion beam of the charged particle beam device according to the embodiment of the present invention, and FIG. 9 is a view showing the tip of the needle 18 in the image data which is obtained by the electron beam. Here, in FIGS. 8 and 9, the reason why the directions of the needle 18 are different from each other is because the positional relationship of the focused ion beam irradiation optical system 14, the electron beam irradiation optical system 15 and the detector 16, and the display direction of the image by secondary electrons are different, and thus, FIGS. 8 and 9 show the situation in which the same needle 18 is differently viewed due to the difference of the observation directions.

In addition, in FIG. 9, two needles 18a and 18b are displayed. However, since the image data of the positions of the tips of the needles before and after the movement in the same visual field is displayed to be overlapped in order to show the situation of the movement of the needle, the needle is the same needle 18.

Moreover, in the above-described processing, the computer 21 moves the position of the tip of the needle 18 into a three-dimensional space toward the movement target position AP using the reference mark Ref and the relative positional relationship among the reference mark Ref, the processing irradiation frame F, and the movement target position AP. However, the present invention is not limited to this. The computer 21 may move the position of the tip of the needle 18 into a three-dimensional space toward the movement target position AP using the relative positional relationship between the reference mark Ref and the movement target position AP without using the processing irradiation frame F.

Next, the computer 21 performs the needle movement (fine adjustment) in which the needle 18 is moved by the needle drive mechanism 19 (Step S10). The computer 21 repeats the pattern matching using the reference image data, and moves the needle 18 while ascertaining the position of the tip of the needle 18. The computer 21 irradiates the needle 18 with the charged particle beam (each of the focused ion beam and the electron beam), and repeatedly acquires the image data by the charged particle beam. The computer 21 performs the pattern matching using the reference image data with respect to the acquired image data, and acquires the position of the tip of the needle 18. The computer 21 moves the needle 18 into the three-dimensional space according to the acquired position of the tip of the needle 18 and the movement target position.

Figure 10:
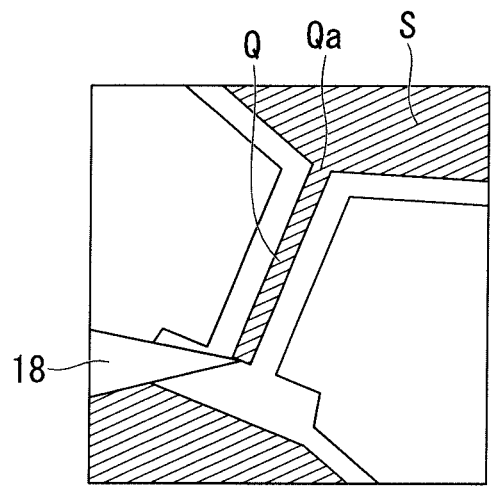
FIG. 10 is a view showing the tip of the needle and the sample piece in the image data which is obtained by the focused ion beam of the automatic sample preparation apparatus according to the embodiment of the present invention.
Figure 11:
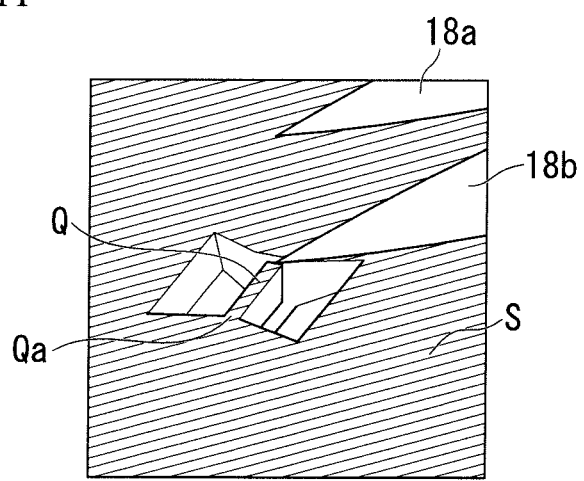
FIG. 11 is a view showing the tip of the needle and the sample piece in the image data which is obtained by the electron beam of the automatic sample preparation apparatus according to the embodiment of the present invention.

Next, the computer 21 performs processing in which the computer 21 stops the movement of the needle 18 (Step S11). The computer 21 moves the needle 18 in a state of irradiating the irradiation region including the movement target position with the charged particle beam, and in a case where the absorption current flowing to the needle 18 exceeds a predetermined current, the computer 21 stops the drive of the needle 18 by the needle drive mechanism 19. Accordingly, the computer 21 disposes the position of the tip of the needle 18 at the movement target position close to the side portion opposite to the support portion Qa among the side portions of the sample piece Q. FIGS. 10 and 11 show this aspect, and are a view (FIG. 10) showing the tip of the needle 18 and the sample piece Q in the image data obtained by the focused ion beam of the automatic sample preparation apparatus 10 according to the embodiment of the present embodiment, and a view (FIG. 11) showing the tip of the needle 18 and the sample piece Q in the image data obtained by the electron beam. In addition, similarly to FIGS. 8 and 9, in FIGS. 10 and 11, the observation directions of the focused ion beam and the electron beam are different from each other, and the observation magnification is different from each other. However, the observation object and the needle 18 are the same observation object and the same needle 18.

Next, the computer 21 performs processing in which the computer 21 connects the needle 18 to the sample piece Q (Step S12). The computer 21 designates a preset connection processing position using the reference mark Ref formed on the sample S. The computer 21 sets the connection processing position to a position away from the sample piece Q by a predetermined gap. The computer 21 sets the upper limit of the predetermined gap to 1 µm, and preferably, sets the predetermined gap to 100 nm or more and 200 nm or less. The computer 21 supplies gas to the sample piece Q and the surface of the tip of the needle 18 by the gas supply portion 17 while irradiating the irradiation region including the processing irradiation frame R1 set to the connection processing position with the focused ion beam over a predetermined time. Accordingly, the computer 21 connects the sample piece Q and the needle 18 to each other by the deposition film.

Figure 12:
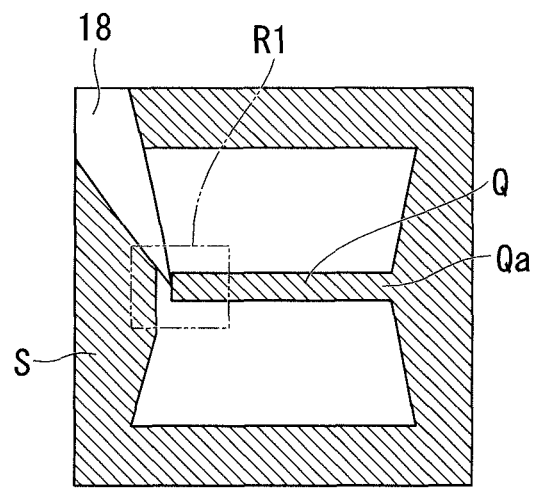
FIG. 12 is a view showing a processing irradiation frame including connection processing positions of the needle and the sample piece in the image data which is obtained by the focused ion beam of the automatic sample preparation apparatus according to the embodiment of the present invention.

In Step S12, since the computer 21 connects the needle 18 and the sample piece Q to each other in a state where the needle 18 does not come into contact with the sample piece Q, an advantage is provided, in which the occurrence of a disadvantage such as damage due to contact can be prevented. In addition, in the subsequent process, when the needle 18 and the sample piece Q are separated from each other by cutting, it is possible to prevent the needle 18 from being cut. In addition, in a case where vibrations of the needle 18 occur, it is possible to prevent the vibrations from being transmitted to the sample piece Q. In addition, even in a case where the movement of the sample piece Q occurs due to a creep phenomenon of the sample S, it is possible to prevent excessive strain from occurring in the portion between the needle 18 and the sample piece Q. FIG. 12 shows this aspect, and is a view showing the processing irradiation frame R1 including the connection processing positions of the needle 18 and the sample piece Q in the image data which is obtained by the focused ion beam of the automatic sample preparation apparatus 10 according to the embodiment of the present invention.

When the needle 18 is connected to the sample piece Q, the computer 21 sets a connection posture suitable for each approach mode selected when the sample piece Q connected to the needle 18 is subsequently transferred to the sample piece holder P. The computer 21 sets the relative connection posture between the needle 18 and the sample piece Q corresponding to each of multiple (for example, three) different approach modes described below.

Moreover, the computer 21 may determine the connection state performed by the deposition film by detecting variation of the absorption currents of the needle 18. In the case where the computer 21 determines the connection between the sample piece Q and the needle 18 performed by the deposition film according to the variation of the absorption currents of the needle 18, the computer may stop the formation of the deposition film regardless of the presence or absence of elapse of a predetermined time.

Figure 13:
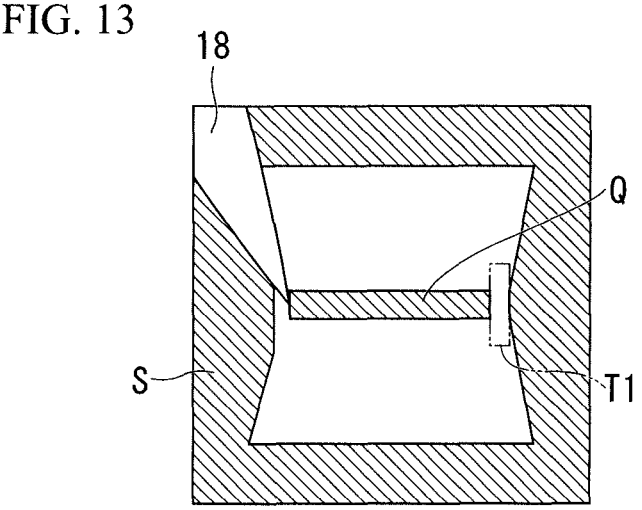
FIG. 13 is a view showing a cutting position T1 of the support portion of the sample and the sample piece in the image data which is obtained by the focused ion beam of the automatic sample preparation apparatus according to the embodiment of the present invention.

Next, the computer 21 performs processing in which the computer 21 cuts the support portion Qa between the sample piece Q and the sample S (Step S13). The computer 21 designates a preset cutting position T1 of the support portion Qa using the reference mark which is formed on the sample S. The computer 21 separates the sample piece Q from the sample S by irradiating the cutting position T1 with the focused ion beam over a predetermined time. FIG. 13 shows this aspect, and is a view showing the cutting position T1 of the support portion Qa of the sample S and the sample piece Q in the image data which is obtained by the focused ion beam of the automatic sample preparation apparatus 10 according to the embodiment of the present invention.

The computer 21 determines whether or not the sample piece Q is separated from the sample S by detecting conduction between the sample S and the needle 18. In a case where the computer 21 detects the conduction between the sample S and the needle 18 after the cutting ends, that is, after the cutting of the support portion Qa between the sample piece Q and the sample S at the cutting position T1 is completed, the computer 21 determines that the sample piece Q is not separated from the sample S. In the case where it is determined that the sample piece Q is not separated from the sample S, the computer 21 informs that the separation between the sample piece Q and the sample S is not completed by display or sound, and stops the performance of the subsequent processing. Meanwhile, in a case where the computer 21 does not detect the conduction between the sample S and the needle 18, the computer 21 determines that the sample piece Q is separated from the sample S, and continues the performance of the subsequent processing.

Figure 14:
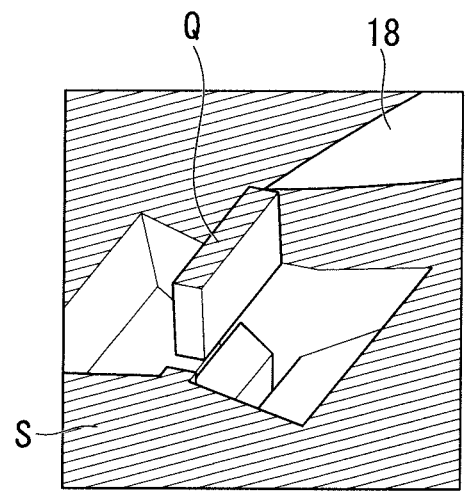
FIG. 14 is a view showing a state where the needle to which the sample piece is connected is retreated in the image data which is obtained by the electron beam of the automatic sample preparation apparatus according to the embodiment of the present invention.

Next, the computer 21 performs the processing in which the computer retreats the needle (Step S14). The computer 21 lifts the needle 18 toward the upper portion in the vertical direction (that is, the positive direction in the Z direction) by a predetermined distance (for example, 5 µm or the like) by the needle drive mechanism 19. FIG. 14 shows this aspect, and is a view showing the state where the needle 18 to which the sample piece Q is connected is retreated in the image data which is obtained by the electron beam of the automatic sample preparation apparatus 10 according to the embodiment of the present invention.

Figure 15:
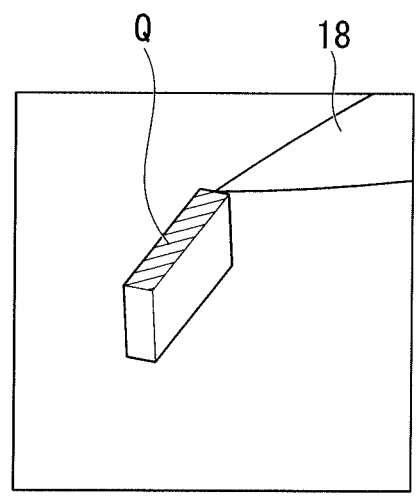
FIG. 15 is a view showing a state where a stage is retreated with respect to the needle, to which the sample piece is connected, in the image data which is obtained by the electron beam of the automatic sample preparation apparatus according to the embodiment of the present invention.

Next, the computer 21 performs processing in which the computer 21 retreats the stage (Step S15). As shown in FIG. 15, the computer 21 lowers the stage 12 toward the lower portion in the vertical direction (that is, the negative direction in the Z direction) by a predetermined distance (for example, 5 mm or the like) by the drive mechanism 13. After the computer 21 lowers the stage 12 by a predetermined distance, the computer 21 lifts the nozzle of the gas supply portion 17 to the standby position above the stage 12 in the vertical direction. FIG. 15 shows this aspect, and is a view showing a state where the stage 12 is retreated with respect to the needle 18, to which the sample piece Q is connected, in the image data which is obtained by the electron beam of the automatic sample preparation apparatus 10 according to the embodiment of the present invention.

(Posture Control Process)

Next, the computer 21 performs a posture control process if necessary. The computer 21 rotates the sample piece Q extracted from the sample S, and fixes the sample piece Q to the sample piece holder P in a state where the upper side and the lower side or the right side and the left side of the sample piece Q are changed. The computer 21 fixes the sample piece Q to the sample piece holder P such that the surface of the sample piece Q corresponding to the surface of the original sample S is perpendicular to the end surface of the columnar portion 34 or is parallel to the end surface of the columnar portion 34. Accordingly, for example, the computer 21 secures the posture of the sample piece Q suitable for finishing processing which is subsequently performed, and can decrease influences of a curtain effects generated when the finishing processing is performed. The computer 21 performs eccentricity correction when the needle 18 rotates, and corrects the rotation such that the sample piece Q is not deviated from an actual visual field.

In addition, the computer 21 performs shape processing of the sample piece Q by the irradiation of the focused ion beam if necessary. Particularly, preferably, the shaping is performed such that the end surface of the sample piece Q after the shaping which is in contact with the columnar portion 34 is approximately parallel to the end surface of the columnar portion 34. The computer 21 performs the shape processing such as a portion of the sample piece Q being cut before template preparation described below. The computer 21 sets the processing position of the shape processing with a distance from the needle 18 as a reference. Accordingly, the computer 21 easily performs edge extraction from a template described below, and secures the shape of the sample piece Q suitable for the finishing processing which is subsequently performed.

In the posture control process, first, the computer 21 drives the needle 18 by the needle drive mechanism 19, and rotates the needle 18 by an angle corresponding to a posture control mode such that the posture of the sample piece Q reaches a predetermined posture (Step S16). Here, the posture control mode is a mode in which the posture of the sample piece Q is controlled to be a predetermined posture. Here, the needle 18 approaches the sample piece Q at a predetermined angle with respect to the sample piece Q, the needle 18 to which the sample piece Q is connected rotates at a predetermined angle, and the posture of the sample piece Q is controlled. The computer 21 performs the eccentricity correction when the needle 18 rotates. FIGS. 16 to 21 show this aspect, and are views showing the state of the needle 18 to which the sample piece Q is connected in each of multiple (for example, three) approach modes different from each other.

Figure 16:
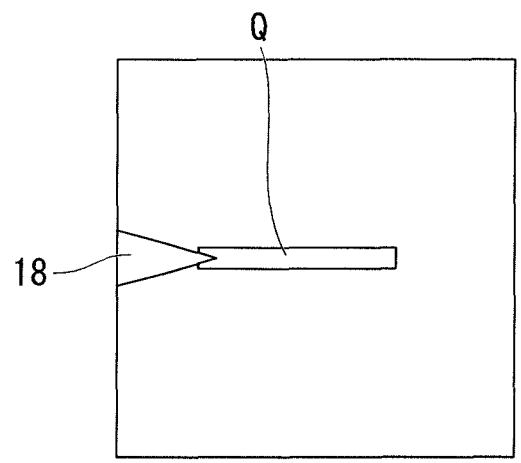
FIG. 16 is a view showing an approach mode state in which a rotation angle of the needle to which the sample piece is connected is 0° in the image data which is obtained by the focused ion beam of the automatic sample preparation apparatus according to the embodiment of the present invention.
Figure 17:
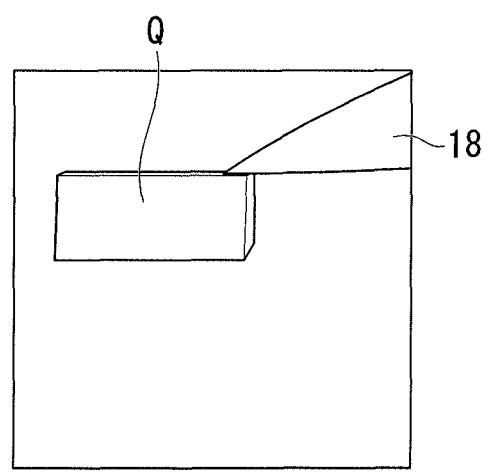
FIG. 17 is a view showing an approach mode state in which a rotation angle of the needle to which the sample piece is connected is 0° in the image data which is obtained by the electron beam of the automatic sample preparation apparatus according to the embodiment of the present invention.

FIGS. 16 and 17 are views showing the state of the needle 18 to which the sample piece Q is connected in an approach mode in which the rotation angle of the needle 18 is 0°. FIG. 16 is a view showing the state of the needle 18 to which the sample piece Q is connected in the image data which is obtained by the focused ion beam of the automatic sample preparation apparatus 10 according to the embodiment of the present invention. FIG. 17 is a view showing the state of the needle 18 to which the sample piece Q is connected in the image data which is obtained by the electron beam of the automatic sample preparation apparatus 10. In the approach mode in which the rotation angle of the needle 18 is 0°, the computer 21 sets the posture state suitable for transferring the sample piece Q to the sample piece holder P without rotating the needle 18.

Figure 18:
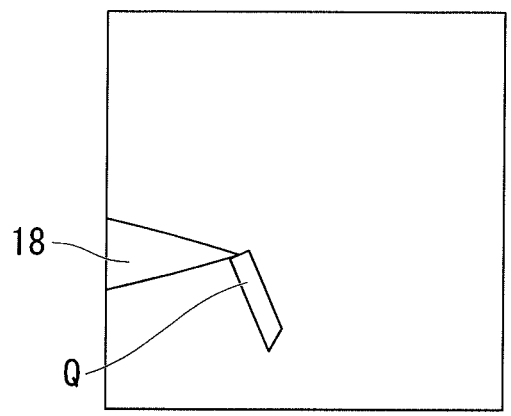
FIG. 18 is a view showing an approach mode state in which a rotation angle of the needle to which the sample piece is connected is 90° in the image data which is obtained by the focused ion beam of the automatic sample preparation apparatus according to the embodiment of the present invention.
Figure 19:
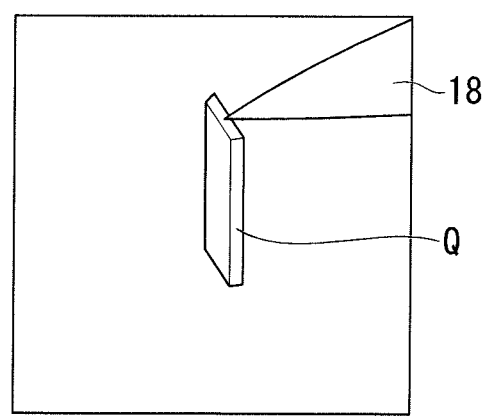
FIG. 19 is a view showing an approach mode state in which the rotation angle of the needle to which the sample piece is connected is 90° in the image data which is obtained by the electron beam of the automatic sample preparation apparatus according to the embodiment of the present invention.

FIGS. 18 and 19 are views showing the state of the needle 18 to which the sample piece Q is connected in an approach mode in which the rotation angle of the needle 18 is 90°. FIG. 18 is a view showing the state where the needle 18 to which the sample piece Q is connected is rotated by 90° in the image data which is obtained by the focused ion beam of the automatic sample preparation apparatus 10 according to the embodiment of the present invention. FIG. 19 is a view showing the state where the needle 18 to which the sample piece Q is connected is rotated by 90° in the image data which is obtained by the electron beam of the automatic sample preparation apparatus 10. In the approach mode in which the rotation angle of the needle 18 is 90°, the computer 21 sets the posture state suitable for transferring the sample piece Q to the sample piece holder P in the state where the needle 18 is rotated by 90°.

Figure 20:
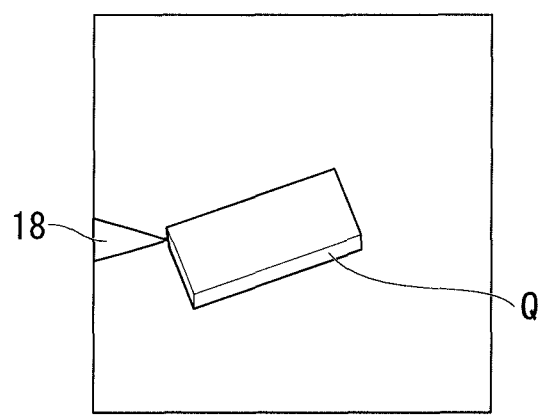
FIG. 20 is a view showing an approach mode state in which the rotation angle of the needle to which the sample piece is connected is 180° in image data which is obtained by the focused beam of a charged particle beam device according to the embodiment of the present invention.
Figure 21:
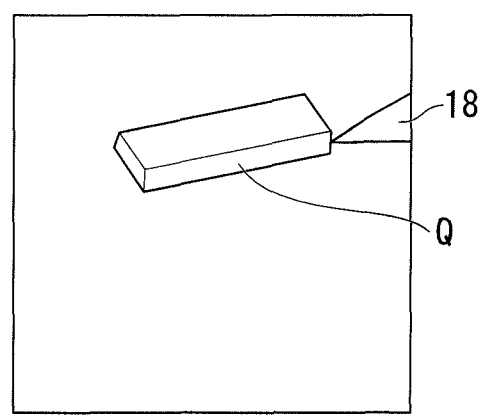
FIG. 21 is a view showing an approach mode state in which the rotation angle of the needle to which the sample piece is connected is 180° in the image data which is obtained by the electron beam of the automatic sample preparation apparatus according to the embodiment of the present invention.

FIGS. 20 and 21 are views showing the state of the needle 18 to which the sample piece Q is connected in an approach mode in which the rotation angle of the needle 18 is 180°. FIG. 20 is a view showing the state where the needle 18 to which the sample piece Q is connected is rotated by 180° in the image data which is obtained by the focused ion beam of the automatic sample preparation apparatus 10 according to the embodiment of the present invention. FIG. 21 is a view showing the state where the needle 18 to which the sample piece Q is connected is rotated by 90° in the image data which is obtained by the electron beam of the automatic sample preparation apparatus 10. In the approach mode in which the rotation angle of the needle 18 is 180°, the computer 21 sets the posture state suitable for transferring the sample piece Q to the sample piece holder P in the state where the needle 18 is rotated by 180°.

In addition, the relative connection posture between the needle 18 and the sample piece Q is set to the connection posture suitable for each approach mode when the needle 18 is connected to the sample piece Q in the above-described sample piece pick-up process.

In Step S16, the computer 21 causes an eccentricity locus of the needle 18 to approximate to an ellipse using the positions of the needle 18 at different angles of at least three points when the needle 18 is rotated around the center axis by a rotation mechanism (not shown) of the needle drive mechanism 19. For example, the computer 21 calculates the change of the positions of the needle 18 at each of different angles of three points or more by sinusoidal waves, and causes the eccentricity locus of the needle 18 to approximate to an ellipse or a circle. In addition, the computer 21 corrects positional deviation of the needle 18 for each predetermined angle using the eccentricity locus of the needle 18.

(Template Preparation Process of Needle and Sample Piece)

Next, the computer 21 performs the template preparation process of the needle and the sample piece. The computer 21 acquires the template while moving the needle 18 to a location at which a structure does not exist on the background of the needle 18 and the sample piece Q connected to each other. Accordingly, when the computer 21 automatically recognizes the edges (outlines) of the needle 18 and the sample piece Q from the image which is obtained by each of the focused ion beam and the electron beam, the computer 21 prevents the edge from being erroneously recognized due to a structure on the backgrounds of the needle 18 and the sample piece Q. The computer 21 prepares the templates of the needle 18 and the sample piece Q in the posture state (that is, the posture in which the sample piece Q is connected to the columnar portion (pillar) 34 of the sample bed 33) in which the needle 18 to which the sample piece Q is fixed is rotated if necessary. Accordingly, the computer 21 three-dimensionally recognizes the edges (outline) of the needle 18 and the sample piece Q from the image data which is obtained by each of the focused ion beam and the electron beam according to the rotation of the needle 18. In addition, in the approach mode in which the rotation angle of the needle 18 is 0°, the computer 21 may recognize the edges (outline) of the needle 18 and the sample piece Q from the image data which is obtained by the focused ion beam without requiring the electron beam.

When the computer 21 instructs the drive mechanism 13 or the needle drive mechanism 19 such that the needle 18 moves to the location at which a structure does not exist on the backgrounds of the needle 18 and the sample piece Q, in a case where the needle 18 is not positioned at the location which is instructed actually, the computer 21 searches the needle 18 in the state where the observation magnification is low magnification. The computer 21 initializes the position coordinate of the needle 18 in a case where the needle 18 is not found, and the computer 21 moves the needle 18 to the initial position.

In the template preparation process, first, the computer 21 acquires a template (reference image data) for template-matching with respect to the shapes of the tips of the sample piece Q and the needle 18 to which the sample piece Q is connected (Step S17). The computer 21 irradiates the needle 18 with the charged particle beam (each of the focused ion beam and the electron beam) while scanning the irradiation position. The computer 21 acquires the image data indicating the position distribution in multiple different planes of the secondary charged particles R emitted from the needle 18 by the irradiation of the charged particle beam. The computer 21 acquires the image data on the XY plane by the irradiation of the focused ion beam, and acquires the image data on the XYZ plane (the plane perpendicular to the optical axis of the electron beam) by the irradiation of the electron beam. The computer 21 stores the image data acquired from two different directions as a template (reference image data).

Since the computer 21 has the image data which is actually acquired with respect to the sample piece Q which is actually formed by the focused ion beam processing and the needle 18 to which the sample piece Q is connected, the computer 21 can perform the pattern matching with high accuracy regardless of the shapes of the sample piece Q and the needle 18.

In addition, when the computer 21 acquires the image data, the computer 21 uses image acquisition conditions such as the magnification, the brightness, or the contrast which are stored in advance in order to increase recognition accuracy with respect to the shapes of the sample piece Q and the needle 18 to which the sample piece Q is connected.

Next, the computer 21 performs processing in which the computer 21 retreats the needle (Step S18). The computer 21 lifts the needle 18 toward the upper portion (that is, the positive direction in the Z direction) in the vertical direction by a predetermined distance by the needle drive mechanism 19.

Figure 22:
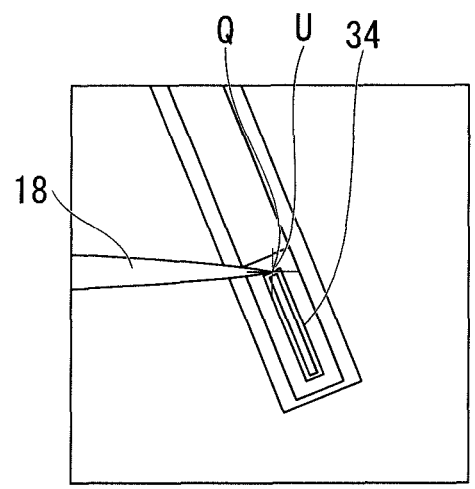
FIG. 22 is a view showing an attachment position of a columnar portion to the sample piece in the image data which is obtained by the focused ion beam of the automatic sample preparation apparatus according to the embodiment of the present invention.
Figure 23:
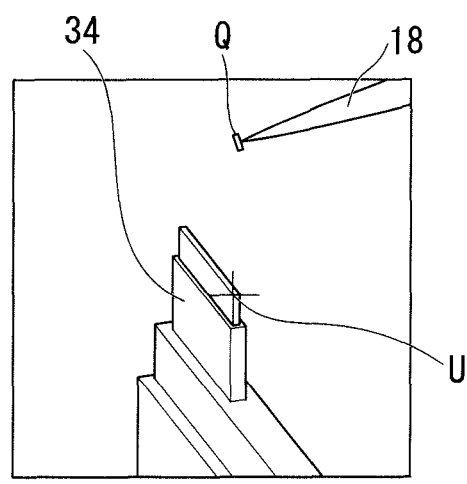
FIG. 23 is a view showing the attachment position of the columnar portion to the sample piece in the image data which is obtained by the electron beam of the automatic sample preparation apparatus according to the embodiment of the present invention.

Next, the computer 21 moves the stage 12 by the drive mechanism 13 such that the position of the sample piece holder P registered in the above-described Step S02 is included in the visual field region (Step S19). FIGS. 22 and 23 show this aspect. FIG. 22 is a view showing an attachment position U of a columnar portion 34 to the sample piece Q in the image data which is obtained by the focused ion beam of the automatic sample preparation apparatus 10 according to the embodiment of the present invention. FIG. 23 is a view showing the attachment position U of the columnar portion 34 to the sample piece Q in the image data which is obtained by the electron beam of the automatic sample preparation apparatus 10.

Next, the computer 21 adjusts the horizontal position of the sample piece holder P while moving the stage 12 by the drive mechanism 13, and rotates the stage 12 by the angle corresponding to the posture control mode such that the posture of the sample piece holder P is a predetermined posture (Step S20). In addition, the computer 21 lowers the nozzle 17a of the gas supply portion 17 from the standby position above the stage 12 in the vertical direction toward the processing position.

(Template-Matching Process of Pillar)

Next, the computer 21 performs a template-matching process of the pillar. The computer 21 performs the template-matching so as to correctly recognize the positions of the multiple columnar portions (pillars) 34 of the comb-tooth shaped sample bed 33. The computer 21 performs the template-matching in the image data obtained by the focused ion beam and the electron beam using the template for each columnar portion (pillar) 34 which is prepared in the template preparation process of the pillar in advance.

In addition, when the computer 21 instructs the drive mechanism 13 such that the stage 12 moves, in a case where the stage 12 does not move to a predetermined position in actual, the computer 21 initializes the position coordinate of the stage 12 so as to move the stage 12 to the initial position.

In addition, in the template-matching for each columnar portion (pillar) 34 which is performed after the stage 12 moves, in a case where a problematic columnar portion (pillar) 34 exists, the computer 21 change the attachment object of the sample piece Q from the problematic columnar portion (pillar) 34 to an adjacent columnar portion (pillar) 34.

In addition, when the computer 21 extracts the edge (outline) from a predetermined region (a region including at least the columnar portion (pillar) 34) of the image data in the template-matching, the computer 21 displays the extracted edge on the display device 20. Since the columnar portion (pillar) 34 has a sharp edge (outline) shown in FIGS. 22 and 23, it is possible to perform the template-matching having high matching accuracy. In addition, when the computer 21 cannot extract the edge (outline) from the predetermined region (a region including at least the columnar portion (pillar) 34) of the image data in the template-matching, the computer 21 acquires the image data again.

In the template-matching process, the computer 21 recognizes the attachment position of the sample piece Q stored in the above-described Step S02 using the image data generated by the irradiation of each of the focused ion beam and the electron beam (Step S21). The computer 21 drives the stage 12 by the drive mechanism 13 such that the attachment position recognized by the irradiation of the electron beam coincides with the attachment position recognized by the irradiation of the focused ion beam. The computer 21 drives the stage 12 by the drive mechanism 13 such that the attachment position U of the sample piece Q coincides with the visual field center (processing center) of the visual field region.

Next, the computer 21 performs the processing of the following Steps S22 to S25 as the processing in which the computer 21 causes the sample piece Q connected to the needle 18 to come into contact with the sample piece holder P.

First, the computer 21 recognizes the position of the needle 18 (Step S22). The computer 21 detects the absorption current flowing to the needle 18 by irradiating the needle 18 with the charged particle beam while scanning the irradiation position, and generates the absorption current image data indicating the two-dimensional position distribution of the absorption current with respect to multiple different planes. The computer 21 acquires the absorption current image data of the XY plane by the irradiation of the focused ion beam, and acquires the image of the XYZ plane (the plane perpendicular to the optical axis of the electron beam) by the irradiation of the electron beam. The computer 21 detects the position of the tip of the needle 18 in a three-dimensional space using the absorption current image data acquired with respect to two different planes.

In addition, the computer 21 drives the stage 12 by the drive mechanism 13 using the detected position of the tip of the needle 18, and may set the position of the tip of the needle 18 to the preset center position (visual field center) of the visual field region.

(Sample Piece Mount Process)

Next, the computer 21 performs a sample piece mount process. First, the computer 21 performs template-matching in order to accurately recognize the position of the sample piece Q connected to the needle 18. The computer 21 performs the template-matching in the image data obtained by the irradiation of each of the focused ion beam and the electron beam, using the templates of the needle 18 and the sample piece Q connected to each other which are prepared in the template preparation process of the needle and the sample piece in advance.

In addition, when the computer 21 extracts the edge (outline) from the predetermined region (the region including at least the needle 18 and the sample piece Q) of the image data in the template-matching, the computer 21 displays the extracted edge on the display device 20. In addition, in a case where the computer 21 cannot extract the edge (outline) from the predetermined region (the region including at least the needle 18 and the sample piece Q) of the image data in the template-matching, the computer 21 acquires the image data again.

In addition, in the image data obtained by the irradiation of each of the focused ion beam and the electron beam, the computer 21 measures the distance between the sample piece Q and the columnar portion (pillar) 34 based on the template-matching which uses the templates of the needle 18 and the sample piece Q connected to each other, and the template of the columnar portion (pillar) 34 which is the attachment object of the sample piece Q.

In addition, finally, the computer 21 transfers the sample piece Q to the columnar portion (pillar) 34 which is the attachment object of the sample piece Q by only the movement in the plane parallel to the stage 12.

In the sample piece mount process, first, the computer 21 performs the needle movement in which the needle 18 is moved by the needle drive mechanism 19 (Step S23). In the image data which is obtained by the irradiation of each of the focused ion beam and the electron beam, the computer 21 measures the distance between the sample piece Q and the columnar portion (pillar) 34 based on the template-matching which uses the templates of the needle 18 and the sample piece Q and the template of the columnar portion (pillar) 34. The computer 21 moves the needle 18 into a three-dimensional space toward the attachment position according to the measured relative distance.

(Sample Piece Mount Detection Process)

Next, the computer 21 performs the sample piece mount process. The computer 21 ends deposition in a case where the conduction between the columnar portion (pillar) 34 and the needle 18 is detected in the process in which the sample piece Q is fixed to the columnar portion (pillar) 34 by the deposition. The computer 21 stops the needle 18 with a gap between the columnar portion (pillar) 34 and the sample piece Q. The computer 21 sets the gap to 1 μm or less, and preferably, sets the gap to 100 nm or more and 200 nm or less. In a case where the gap is 500 nm or more, a time required for connecting the columnar portion (pillar) 34 and the sample piece Q to each other by the deposition film is lengthened to a predetermined value or more. The time required for connecting the columnar portion (pillar) 34 and the sample piece Q to each other by the deposition film decreases as the gap decreases.

In addition, when the gap is provided, after the computer 21 causes the sample piece Q to come into contact with the columnar portion (pillar) 34 once, the computer 21 may provide the gap. In addition, instead of the computer 21 detecting the conduction between the columnar portion (pillar) 34 and the needle 18, the computer 21 may provide the gap by detecting the absorption current images of the columnar portion (pillar) 34 and the needle 18.

After the computer 21 transfers the sample piece Q to the columnar portion (pillar) 34 by detecting the conduction between the columnar portion (pillar) 34 and the needle 18 or the absorption current images of the columnar portion (pillar) 34 and the needle 18, the computer 21 detects the presence or absence of the separation between the sample piece Q and the needle 18.

In addition, in a case where the computer 21 cannot detect the conduction between the columnar portion (pillar) 34 and the needle 18, the computer 21 switches the processing to processing in which the absorption current images of the columnar portion (pillar) 34 and the needle 18 are detected.

Moreover, in the case where the computer 21 cannot detect the conduction between the columnar portion (pillar) 34 and the needle 18, the computer 21 stops the transfer of the sample piece Q, separates the sample piece Q from the needle 18, and may perform a needle-trimming process described below.

Figure 24:
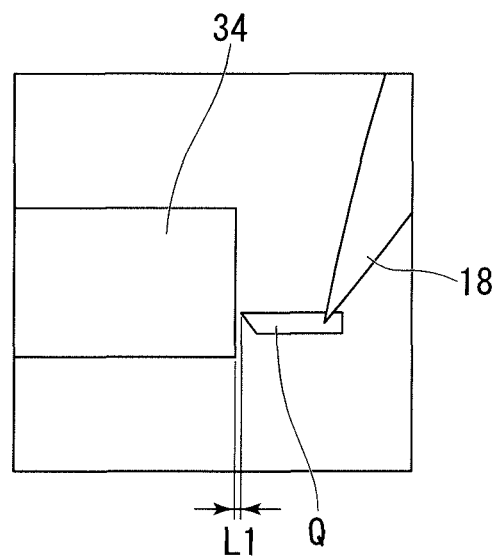
FIG. 24 is a view showing the needle which movement stops around the attachment position of the sample piece of a sample bed in the image data which is obtained by the focused ion beam of the automatic sample preparation apparatus according to the embodiment of the present invention.
Figure 25:
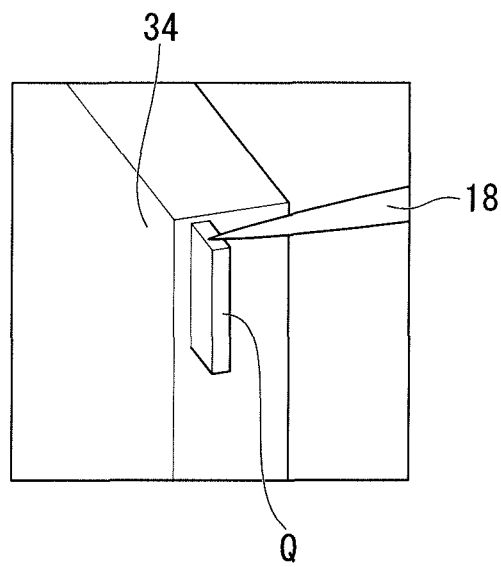
FIG. 25 is a view showing the needle which movement stops around the attachment position of the sample piece of the sample bed in the image data which is obtained by the electron beam of the automatic sample preparation apparatus according to the embodiment of the present invention.

In the sample piece mount detection process, first, the computer 21 performs processing in which the computer 21 stops the movement of the needle 18 (Step S24). FIGS. 24 and 25 show this aspect. FIG. 24 is a view showing the needle 18 in which the movement of the needle 18 stops around the attachment position U of the sample piece Q of the columnar portion 34 in the image data which is obtained by the focused ion beam of the automatic sample preparation apparatus 10 according to the embodiment of the present invention. FIG. 25 is a view showing the needle 18 in which the movement of the needle 18 stops around the attachment position U of the sample piece Q of the columnar portion 34 in the image data which is obtained by the electron beam of the automatic sample preparation apparatus 10 according to the embodiment of the present invention. Here, since the upper end portion of the sample piece Q in appearance is positioned to be arranged on the upper end portion of the columnar portion (pillar) 34, this is suitable for a case where the sample piece Q is additionally processed in the subsequent process. The movement of the needle 18 shown in FIG. 24 is stopped so as to provide a distance L1 from the side surface of the columnar portion (pillar) 34 to the sample piece Q.

Figure 26:
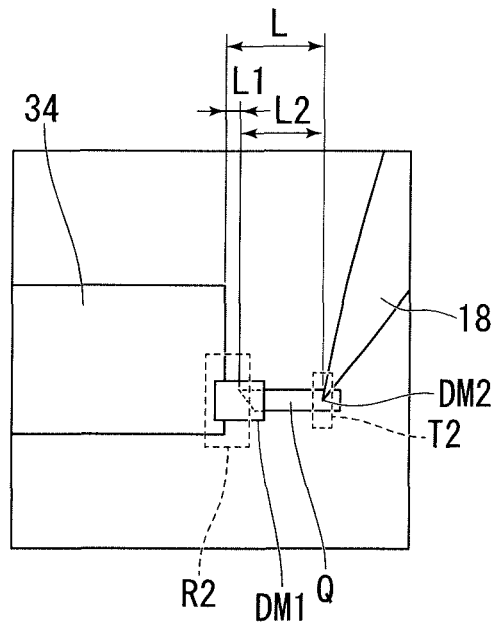
FIG. 26 is a view showing the processing irradiation frame for connecting the sample piece connected to the needle to the sample bed in the image data which is obtained by the focused ion beam of the automatic sample preparation apparatus according to the embodiment of the present invention.

Next, the computer 21 performs the processing in which the computer 21 connects the sample piece Q connected to the needle 18 to the columnar portion (pillar) 34 (Step S25). The computer 21 sets the processing irradiation frame R2 so as to include the edge of the columnar portion (pillar) 34 at which the attachment position of the sample piece Q is set. The computer 21 irradiates the irradiation region including the processing irradiation frame R2 with the focused ion beam over a predetermined time while supplying gas to the surfaces of the sample piece Q and the columnar portion (pillar) 34 by the gas supply portion 17. FIG. 26 shows this aspect, and is a view showing the processing irradiation frame R2 for connecting the sample piece Q connected to the needle 18 to the columnar portion (pillar) 34 in the image data which is obtained by the focused ion beam of the automatic sample preparation apparatus 10 according to the embodiment of the present invention.

In addition, the computer 21 may determine the connection state performed by a deposition film DM1 by detecting the change of the absorption currents of the needle 18. In a case where the computer 21 determines that the sample piece Q and the columnar portion (pillar) 34 are connected to each other by the deposition film DM1 according to the change of the absorption currents of the needle 18, the computer 21 may stop the formation of the deposition film DM1 regardless of the presence or absence of elapse of the predetermined time.

Next, the computer 21 performs processing in which the computer 21 cuts the deposition film DM2 which connects the needle 18 and the sample piece Q to each other (Step S26). FIG. 26 shows this aspect, and is a view showing a cutting position T2 for cutting the deposition film DM2 which connects the needle 18 and the sample piece Q to each other in the image data which is obtained by the focused ion beam of the automatic sample preparation apparatus 10 according to the embodiment of the present invention. The computer 21 sets a position which is separated from the side surface of the columnar portion (pillar) 34 by a predetermined distance (that is, the sum of the distance L1 from the side surface of the columnar portion (pillar) 34 to the sample piece Q and the size L2 of the sample piece Q) L to the cutting position T2.

Figure 27:
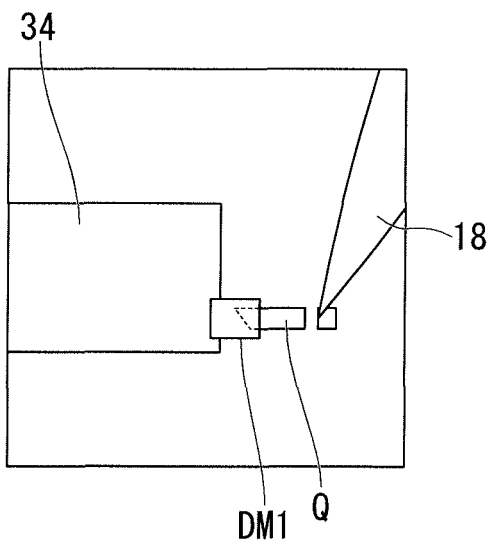
FIG. 27 is a view showing a cutting position at which a deposition film for connecting the needle and the sample piece to each other is cut in the image data which is obtained by the focused ion beam of the automatic sample preparation apparatus according to the embodiment of the present invention.

The computer 21 separates the needle 18 from the sample piece Q by irradiating the cutting position T2 with the focused ion beam over a predetermined time. FIG. 27 shows this aspect, and is a view showing a state where the needle 18 is separated from the sample piece Q in the image data which is obtained by the focused ion beam of the automatic sample preparation apparatus 10 according to the embodiment of the present invention.

In addition, when the computer 21 separates the needle 18 from the sample piece Q, instead of the computer 21 cutting the deposition film DM2 which connects the needle 18 and the sample piece Q to each other, the computer 21 may cut a portion of the sample piece Q. The computer 21 may separate the deposition film DM2 and the needle 18 from the sample piece Q (that is, portions other than the cut portion) along with a portion of the sample piece Q.

The computer 21 determines whether or not the needle 18 is separated from the sample piece Q by detecting the conduction between the sample piece holder P and the needle 18. After the cutting ends, that is, the cutting of the deposition film between the needle 18 and the sample piece Q at the cutting position T2 is completed, in the case where the conduction between the sample piece holder P and the needle 18 is detected, the computer 21 determines that the needle 18 is not separated from the sample bed 33. In the case where the computer 21 determines that the needle 18 is not separated from the sample piece holder P, the computer 21 informs that the separation between the needle 18 and the sample piece Q is not completed by display or sound, and stops the performance of the subsequent processing. Meanwhile, in the case where the conduction between the sample piece holder P and the needle 18 is not detected, the computer 21 determines that the needle 18 is separated from the sample piece Q and continues the performance of the subsequent processing.

Figure 28:
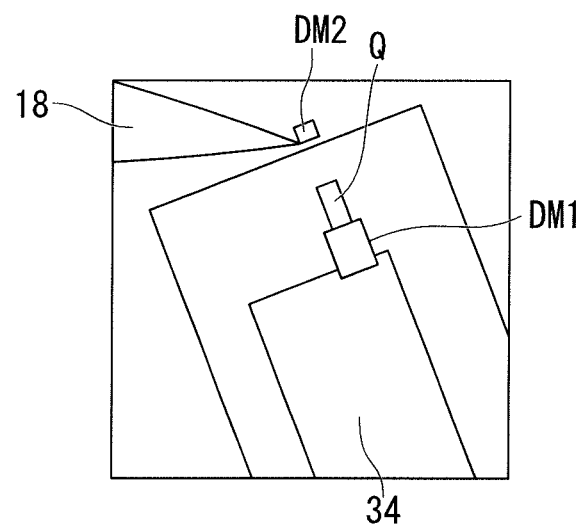
FIG. 28 is a view showing a state where the needle is retreated in the image data which is obtained by the focused ion beam of the automatic sample preparation apparatus according to the embodiment of the present invention.
Figure 29:
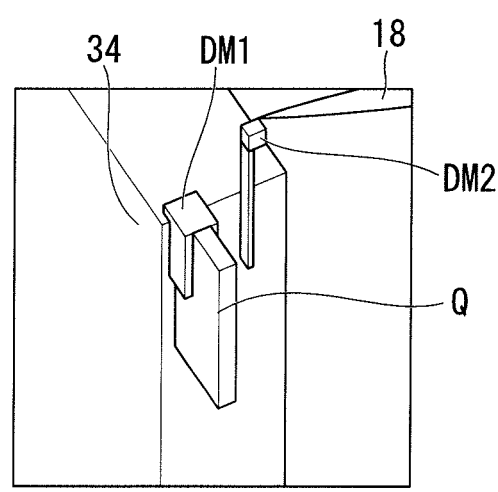
FIG. 29 is a view showing a state where the needle is retreated in the image data which is obtained by the electron beam of the automatic sample preparation apparatus according to the embodiment of the present invention.

Next, the computer 21 performs the processing in which the computer 21 retreats the needle (Step S27). The computer 21 lifts the needle 18 toward the upper portion (the positive direction in the Z direction) in the vertical direction by a predetermined distance (for example, 5 μm or the like) by the needle drive mechanism 19. FIGS. 28 and 29 show this aspect, and are an image (FIG. 28) in which the state where the needle 18 is retreated upward from the sample piece Q is obtained by the focused ion beam of the automatic sample preparation apparatus 10 according to the embodiment of the present invention, and an image (FIG. 29) in which the state is obtained by the electron beam.

Next, the computer 21 performs the processing in which the computer 21 retreats the stage (Step S28). The computer 21 lowers the stage 12 toward the lower portion (that is, the negative direction in the Z direction) in the vertical direction by a predetermined distance (for example, 5 mm or the like) by the drive mechanism 13. After the computer 21 lowers the stage 12 by a predetermined distance, the computer 21 causes the nozzle 17a of the tip of the gas supply portion 17 to be away from the current position.

(Needle-Trimming Process)

Next, the computer 21 performs the needle-trimming process. After the computer 21 performs sampling in the automatic sampling, that is, after the computer 21 separates the sample piece Q separated and extracted from the sample S by the needle 18 from the needle 18, the computer 21 performs trimming of the needle 18. Accordingly, the computer 21 repeatedly uses the needle 18 when the computer 21 separates and extracts the sample piece Q from the sample S. The computer 21 removes the deposition film DM2 attached to the needle 18 by etching using the focused ion beam. The computer 21 performs the template-matching in the image data which is obtained by the irradiation of each of the focused ion beam and the electron beam using the template of the needle 18 which is prepared in the template preparation process of the needle in advance. After the computer 21 moves the needle 18 to the location at which a structure does not exist on the background of the needle 18, the computer 21 acquires the image data by the irradiation of each of the focused ion beam and the electron beam.

In addition, when the computer 21 extracts the edge (outline) from the predetermined region (the region including at least the tip of the needle 18) of the image data in the template-matching, the computer 21 displays the extracted edge on the display device 20.

Moreover, in a case where abnormality occurs in the processing of the template-matching, after the computer 21 initializes the position coordinate of the needle 18 and moves the needle 18 to the initial position, the computer 21 moves the needle 18 to the location at which a structure does not exist on the background of the needle 18. In addition, in a case where abnormality occurs in the processing of the template-matching after the computer 21 initializes the position coordinate of the needle 18, the computer 21 determines that abnormality such as deformation occurs in the shape of the needle 18, the computer 21 ends the automatic sampling.

The computer 21 may perform the needle-trimming process every time the automatic sampling is performed, and the computer 21 stabilizes the processing of the automatic sampling by performing the needle-trimming process periodically. Since the needle-trimming process is provided, it is possible to repeatedly perform the sample sampling without exchanging the needle 18. Accordingly, it is possible to continuously perform sampling on the multiple sample pieces Q using the same needle 18.

Figure 30:
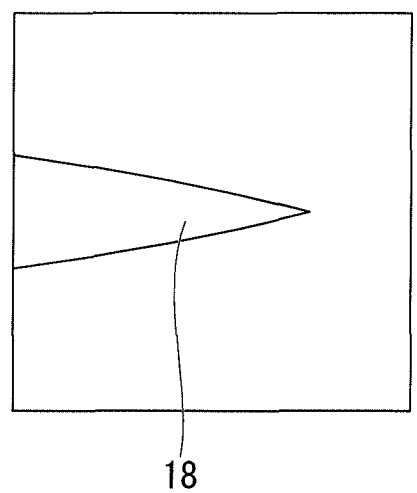
FIG. 30 is a view showing the shape of the tip of the needle in the image data which is obtained by the focused ion beam of the automatic sample preparation apparatus according to the embodiment of the present invention.
Figure 31:
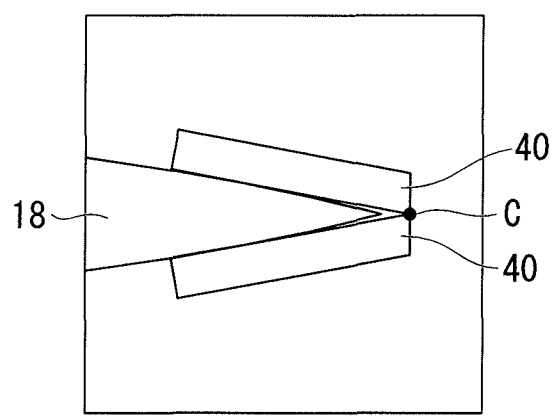
FIG. 31 is a view showing the shape of the tip of the needle in the image data which is obtained by the electron beam of the automatic sample preparation apparatus according to the embodiment of the present invention.

In the needle-trimming process, after the computer 21 image-recognizes the position of the tip of the needle 18 using the image data generated by the irradiation of each of the focused ion beam and the electron beam, the computer 21 sharpens the tip of the needle 18 (Step S29). The computer 21 rotates the needle 18 around the center axis by the rotation mechanism of the needle drive mechanism 19, and performs etching at multiple specific rotation positions different from each other. The computer 21 performs the image-recognition of the shape of the tip of the needle 18 by the pattern matching performed by the reference image acquired at the above-described Step S08, the detection of the edge, or the like. The computer 21 sets a processing frame 40 such that the shape of the tip of the needle 18 becomes a predetermined ideal shape which is set in advance according to the image-recognition of the shape of the tip of the needle 18, and the computer 21 performs etching according to the processing frame 40. The processing frame 40 set the ideal position C, for example, by linearly approximating from the tip of the needle 18 to the base end side portion or the like. FIGS. 30 and 31 show this aspect, FIG. 30 shows the shape of the tip of the needle 18 in the image data obtained by the focused ion beam of the automatic sample preparation apparatus 10 according to the embodiment of the present invention, and FIG. 31 shows the shape of the tip of the needle 18 in the image data obtained by the electron beam.

The computer 21 causes the shape of the tip of the needle 18 to coincide with the predetermined ideal shape which is set in advance, and when the computers 21 drives the needle 18 into a three-dimensional space or the like, the computer 21 can easily recognize the needle 18 by the pattern matching and can accurately detect the position of the needle 18 in the three-dimensional space.

Next, the computer 21 moves the needle 18 to the initial set position by the needle drive mechanism 19 (Step S30).

Hereinbefore, the operation of the automatic sampling ends.

The computer 21 continuously performs Step 01 to Step 30, and the computer 21 can perform the sampling operation in an unmanned manner. Unlike the related art, the sample piece Q can be prepared without a manual operation by an operator.

As described above, according to the automatic sample preparation apparatus 10 of the embodiment of the present invention, since the beam irradiation optical systems 14 and 15, the drive mechanisms 13 and 19, and the gas supply portion 17 are controlled based on the templates of at least the sample piece holder P, the needle 18, and the sample piece Q acquired in advance, it is possible to appropriately automize the operation of transferring the sample piece Q to the sample piece holder P.

In addition, since the template is prepared from the image which is acquired by the irradiation of the charged particle beam in the state where a structure does not exist on the backgrounds of at least the sample piece holder P, the needle 18, and the sample piece Q, it is possible to improve reliability of the template. Accordingly, it is possible to improve accuracy of the template-matching using the template, and it is possible to accurately transfer the sample piece Q to the sample piece holder P based on the positional information which is obtained by the template-matching.

In addition, since the columnar portion (pillar) 34 of the sample bed 33 which is formed by the MEMS process has a sharp edge (outline), it is possible to perform the template-matching having high matching accuracy.

In addition, when instruction is performed such that a structure does not exist on the backgrounds of at least the sample piece holder P, the needle 18, and the sample piece Q, in a case where it is not in the state as the instruction in actual, the positions of at least the sample piece holder P, the needle 18, and the sample piece Q are initialized. Accordingly, it is possible to return the state of each of the drive mechanisms 13 and 19 to a normal state.

In addition, since the template is prepared according to the posture when sample piece Q is transferred to the sample piece holder P, it is possible to improve the positional accuracy when the transfer is performed.

Moreover, since the mutual distance is measured based on the template-matching using the templates of at least the sample piece holder P, the needle 18, and the sample piece Q, it is possible to further improve the positional accuracy when the transfer is performed.

In addition, since the image data is acquired again in a case where the edge cannot be extracted with respect to the predetermined region in the image data of at least the sample piece holder P, the needle 18, and the sample piece Q, it is possible to accurately prepare the template.

Moreover, finally, since the sample piece Q can be transferred to the predetermined position of the sample piece holder P by only the movement in the plane parallel to the stage 12, it is possible to appropriately perform the transfer of the sample piece Q.

In addition, since the shape processing is performed on the sample piece Q held by the needle 18 before the template is prepared, it is possible to improve accuracy of the edge extraction when the template is prepared, and it is possible to secure the shape of the sample piece Q suitable for the finishing process which is subsequently performed. In addition, since the position of the shape processing is set according to the distance from the needle 18, it is possible to accurately perform the shape processing.

In addition, when the needle 18 holding the sample piece Q is rotated so as to have a predetermined posture, it is possible to correct the positional deviation of the needle 18 by eccentricity correction.

Moreover, according to the automatic sample preparation apparatus 10 of the embodiment of the present invention, the computer 21 detects the relative position of the needle 18 with respect to the reference mark Ref when the sample piece Q is formed. Accordingly, it is possible to ascertain the relative positional relationship of the needle 18 with respect to the sample piece Q. The computer 21 sequentially detects the relative position of the needle 18 with respect to the position of the sample piece Q, and the computer 21 can appropriately (that is, without coming into contact with other members, devices, or the like) drive the needle 18 into a three-dimensional space.

In addition, the computer 21 uses the image data which is acquired from at least two different directions, and the computer 21 can accurately ascertain the position of the needle 18 in a three-dimensional space. Accordingly, the computer 21 can appropriately drive the needle 18 in a three-dimensional manner.

In addition, the computer 21 has the image data, which is generated in actual immediately before the computer 21 moves the needle 18, as the template (reference image data). Accordingly, the computer 21 can perform template-matching with high matching accuracy regardless of the shape of the needle 18. Accordingly, the computer 21 can accurately ascertain the position of the needle 18 in a three-dimensional space, and can appropriately drive the needle 18 in a three-dimensional space. Moreover, since the computer 21 acquires the image data in the state where the stage 12 is retreated and a complicated structure does not exist on the background of the needle 18, the computer 21 can acquire the template (reference image data) capable of clearly ascertaining the shape of the needle 18 in a state where influences of the background are excluded.

In addition, since the computer 21 connects the needle 18 and the sample piece Q to each other by the deposition film in the state where the needle 18 and the sample piece Q are not in contact with each other, it is possible to prevent the needle 18 from being cut when the needle 18 and the sample piece Q are separated from each other in the subsequent process. In addition, in the case where vibrations of the needle 18 occur, it is possible to prevent the vibrations from being transmitted to the sample piece Q. Moreover, even in the case where the movement of the sample piece Q occurs due to a creep phenomenon of the sample S, it is possible to prevent excessive strain from occurring in the portion between the needle 18 and the sample piece Q.

In addition, since the gas supply portion 17 supplies deposition gas containing platinum, tungsten, or the like, it is possible to form a deposition film which has a thin film thickness and are dense. Accordingly, even in a case where the needle 18 and the sample piece Q are cut by etching in the subsequent process, it is possible to improve process efficiency by the deposition film having a thin film thickness.

In addition, in a case where the computer 21 cuts the connection between the sample S and the sample piece Q by etching using the irradiation of the focused ion beam, the computer 21 can confirm whether or not the cutting is completed in actual by detecting the presence or absence of conduction between the sample S and the needle 18.

In addition, since the computer 21 informs that the separation between the sample S and the sample piece Q is not completed in actual, even in a case where performance of a series of processes which are automatically performed subsequently to this process is stopped, an operator can easily recognize the reasons for this stopping.

Moreover, in the case where the conduction between the sample S and the needle 18 is detected, the computer 21 determines that cutting of the connection between the sample S and the sample piece Q is not completed in actual, the computer 21 cuts the connection between the sample piece Q and the needle 18 in order to prepare for the driving such as the retreat of the needle 18 subsequently to this process. Accordingly, the computer 21 can prevent the occurrence of disadvantages such as the positional deviation of the sample S or the damage of the needle 18 generated in accordance with the driving of the needle 18.

In addition, the computer 21 can drive the needle 18 after confirming the cutting of the connection between the sample S and the sample piece Q being completed in actual by detecting the presence or absence of the conduction between the sample S and the needle 18. Accordingly, the computer 21 can prevent the occurrence of disadvantages such as the positional deviation of the sample S or the damage of the needle 18 generated in accordance with the driving of the needle 18.

In addition, since the computer 21 has the actual image data with respect to the needle 18 to which the sample piece Q is connected as the template (reference image data), the computer 21 can perform the template-matching with high matching accuracy regardless of the shape of the needle 18 connected to the sample piece Q. Accordingly, the computer 21 can accurately ascertain the position of the needle 18 connected to the sample piece Q in a three-dimensional space, and can appropriately drive the needle 18 and the sample piece Q into the three-dimensional space.

In addition, since the computer 21 extracts the positions of the multiple columnar portions 34 configuring the sample bed 33 using the known template of the sample bed 33, the computer 21 can confirm whether or not the sample bed 33 exists in an appropriate state before the needle 18 is driven.

Moreover, the computer 21 can indirectly and accurately ascertain the needle 18 and the sample piece Q reaching the vicinity of the movement target position according to the changes of the absorption currents before and after the needle 18 to which the sample piece Q is connected reaches the irradiation region. Accordingly, the computer 21 stops the needle 18 and the sample piece Q without coming into contact with other members such as the sample bed 33 which exists at the movement target position, and it is possible to prevent disadvantage such as damage due to contact from occurring.

Moreover, since the computer 21 detects the presence or absence of the conduction between the sample bed 33 and the needle 18 in the case where the sample piece Q and the sample bed 33 are connected to each other by the deposition film, it is possible to accurately confirm whether or not the connection between the sample piece Q and the sample bed 33 is completed in actual.

In addition, the computer 21 can cut the connection between the sample piece Q and the needle 18 after confirming the connection between the sample bed 33 and the sample piece Q being completed in actual by detecting the presence or absence of the conduction between the sample bed 33 and the needle 18.

Moreover, the computer 21 causes the actual shape of the needle 18 to coincide with an ideal reference shape. Accordingly, when the computer 21 drives the needle 18 into a three-dimensional space, or the like, the computer 21 can easily recognize the needle 18 by pattern matching and can accurately detect the position of the needle 18 in the three-dimensional space.

Hereinafter, a first modification example of the above-described embodiment will be described.

In the above-described embodiment, the needle drive mechanism 19 is integrally provided with the stage 12. However, the present invention is not limited to this. The needle drive mechanism 19 may be independently provided from the stage 12. For example, the needle drive mechanism 19 is fixed to the sample chamber 11 or the like. Accordingly, the needle drive mechanism 19 may be independently provided from the tilt driving or the like of the stage 12.

Hereinafter, a second modification example of the above-described embodiment will be described.

In the above-described embodiment, the optical axis of the focused ion beam irradiation optical system 14 is positioned in the vertical direction, and the optical axis of the electron beam irradiation optical system 15 is positioned in the direction inclined to the vertical direction. However, the present invention is not limited to this. For example, the optical axis of the focused ion beam irradiation optical system 14 may be positioned in the direction inclined to the vertical direction, and the optical axis of the electron beam irradiation optical system 15 may be positioned in the vertical direction.

Hereinafter, a third modification example of the above-described embodiment will be described.

In the above-described embodiment, the configuration is provided, in which two kinds of beams such as the focused ion beam irradiation optical system 14 and the electron beam irradiation optical system 15 serving as the charged particle beam irradiation optical system can be emitted. However, the present invention is not limited to this. For example, the electron beam irradiation optical system 15 is not provided, and only the focused ion beam irradiation optical system 14 which is provided in the vertical direction may be provided.

In the above-described embodiment, in some steps described above, the electron beam and the focused ion beam are irradiated to the sample piece holder P, the needle 18, the sample piece Q, or the like in the directions different from each other, the image is acquired by the electron beam, and the image is acquired by the focused ion beam. In the above-described embodiment, the positions of the sample piece holder P, the needle 18, the sample piece Q, or the like and the positional relationships therebetween are ascertained based on the images of the electron beam and the focused beam. However, the positions and the positional relationships may be ascertained by only the image of the focused ion beam.

For example, in a case where the positional relationship between the sample piece holder P and the sample piece Q is ascertained in Step S22, the image is acquired by the focused ion beam such that both the sample piece holder P and the sample piece Q are positioned in the same visual field in a case where the inclination of the stage 12 is horizontal and inclined from the horizontal state by a specific inclination angle. It is possible to ascertain the three-dimensional positional relationship between the sample piece holder P and the sample piece Q from the image in the case where the inclination of the stage 12 is horizontal and the image in the case where the inclination of the stage 12 is inclined from the horizontal state by a specific inclination angle. As described above, since the needle drive mechanism 19 can integrally move in the horizontal direction and the vertical direction with the stage 12, and the needle drive mechanism 19 can be integrally inclined with the stage 12, the relative positional relationship between the sample piece holder P and the sample piece Q is secured regardless of the horizontal state and the inclined state of the stage 12. Accordingly, even when the charged particle beam irradiation optical system has only the focused ion beam irradiation optical system 14, it is possible to observe and process the sample piece Q in two directions different from each other.

Similarly, the registration of the image data of the sample piece holder P in Step S02, the recognition of the needle position in Step S07, the acquisition of the template (reference image) of the needle in Step S08, the acquisition of the reference image of the needle 18 to which the sample piece Q is connected in Step S17, the reorganization of the attachment position of the sample piece Q in Step S21, and the stopping of the needle movement in Step S25 may be similarly performed.

Moreover, in the connection between the sample piece Q and the sample piece holder P in Step S25, the sample piece holder P and the sample piece Q are connected by forming the deposition film on the upper end surfaces of the sample piece holder P and the sample piece Q in the state where the stage 12 is horizontal, the deposition film can be formed in different directions by inclining the stage 12, and it is possible to reliably connect the sample piece holder P and the sample piece Q.

Hereinafter, a fourth modification example of the above-described embodiment will be described.

In the above-described embodiment, the computer 21 automatically performs a series of processing of Step S01 to Step S30 as the operation of the automatic sampling. However, the present invention is not limited to this. The computer 21 may switch the processing such that at least one processing of Step S01 to Step S30 is manually performed by the operator.

In addition, in a case where the operation of the automatic sampling is performed on multiple sample pieces Q, the computer 21 may perform the operation of the automatic sampling on one sample piece Q every time any one of the multiple sample pieces Q is formed on the sample S. In addition, after all of the multiple sample pieces Q are formed on the sample S, the computer 21 may perform the operation of the automatic sampling on each of the multiple sample pieces Q.

In the case where the automatic sampling is performed every time one sample piece Q is formed, it is possible to perform the formation of the sample piece Q and the movement of the needle 18 based on the reference mark Ref without moving (for example, the inclination of the stage 12 or the like) the stage 12. Since the formation of the sample piece Q and the movement of the needle 18 are performed without moving the stage 12, it is possible to prevent the positional deviation and recognition errors of the reference mark Ref from occurring. In addition, even in a case where interruption occurs due to abnormality or the like of the automatic sampling, it is possible to prevent the occurrence of the sample piece Q which is not subjected to the sampling.

Hereinafter, a fifth modification example of the above-described embodiment will be described.

In the above-described embodiment, the computer 21 extracts the position of the columnar portion (pillar) 34 using the known template of the columnar portion (pillar) 34. However, a reference pattern which is prepared from the actual image data of the columnar portion (pillar) 34 in advance may be used as the template. In addition, the computer 21 may use the pattern which is prepared when the automatic processing forming the sample bed 33 is performed as the template.

In addition, in the above-described embodiment, the computer 21 may ascertain the relative relationship of the position of the needle 18 with respect to the position of the sample bed 33, using the reference mark Ref which is formed by the irradiation of the charged particle beam when the columnar portion (pillar) 34 is prepared. The computer 21 sequentially detects the relative position of the needle 18 with respect to the position of the sample bed 33, and can appropriately (that is, without coming into contact with other members, devices, or the like) drive the needle 18 into a three-dimensional space.

Hereinafter, a sixth modification example of the above-described embodiment will be described.

In the above-described embodiment, after the computer 21 moves the sample piece Q connected to the needle 18 to the attachment position, the computer 21 supplies gas to the surfaces of the sample piece Q and the sample bed 33 by the gas supply portion 17. However, the present invention is not limited to this.

Before the sample piece Q connected to the needle 18 reaches the target position around the attachment position, the computer 21 may supply gas to the irradiation region by the gas supply portion 17.

Since the computer 21 can form the deposition film on the sample piece Q in the state where the sample piece Q connected to the needle 18 moves toward the attachment position, it is possible to prevent the sample piece Q from being etched by the focused ion beam. Moreover, the computer 21 can connect the sample piece Q and the sample bed 33 to each other by a deposition film at the time when the sample piece Q reaches the target position around the attachment position.

Hereinafter, a seventh modification example of the above-described embodiment will be described.

In the above-described embodiment, the computer 21 performs etching at a specific rotation position while rotating the needle 18 around the center axis. However, the present invention is not limited to this.

The computer 21 performs etching by the irradiation of the focused ion beam in multiple directions different from each other according to the tilt (rotation around the X axis or the Y axis) of the stage 12 by the tilt mechanism 13b of the drive mechanism 13.

Hereinafter, an eighth modification example of the above-described embodiment will be described.

In the above-described embodiment, in the operation of the automatic sampling, the computer 21 sharpens the tip of the needle 18 every time. However, the present invention is not limited to this.

The computer 21 may perform the sharpening processing of the needle 18 at an appropriate timing in a case where the operations of the automatic sampling are repeatedly performed, for example, at every predetermined number of times of repeated performances or the like.

Moreover, in the above-described embodiment, the computer 21 performs the needle-trimming process after the retreat processing of the stage (Step S28) is performed. However, the present invention is not limited to this.

For example, a timing before the sample piece Q is initially transferred by the needle 18, that is, before the template preparation process (Step S08) of the needle 18, or the like, the computer 21 image-recognizes the shape of the tip of the needle 18, and the computer 21 may sharpens the tip of the needle 18 in a case where the sharpening of the tip is required.

Hereinafter, a ninth modification example of the above-described embodiment will be described.

The processing from Step S22 to Step S25 in which the sample piece Q is connected to the sample piece holder P in the above-described embodiment may be performed as follows. That is, the computer 21 obtains the positional relationship (the distance therebetween) between the columnar portion 34 of the sample piece holder P and the sample piece Q, and the computer 21 operates the needle drive mechanism 19 such that the distance becomes a target value.

Figure 32:
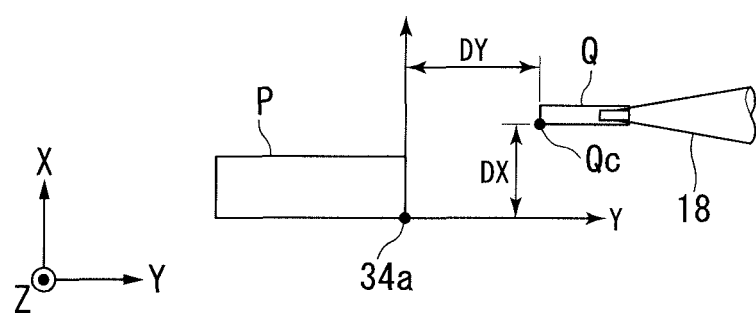
FIG. 32 is an explanatory view showing a positional relationship between the columnar portion and the sample piece based on the image which is obtained by focused ion beam irradiation in the automatic sample preparation apparatus according to the embodiment of the present invention.
Figure 33:
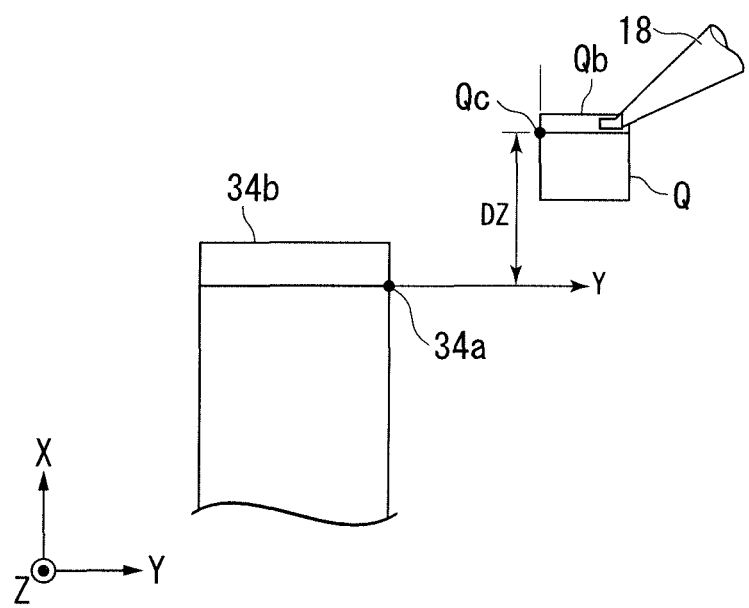
FIG. 33 is an explanatory view showing a positional relationship between the columnar portion and the sample piece based on the image which is obtained by electron beam irradiation in the automatic sample preparation apparatus according to the embodiment of the present invention.

In Step 22, the computer 21 recognizes the positional relationship from the secondary particle image data or the absorption current image data of the needle 18, the sample piece Q, and the columnar portion 34 by the electron beam and the focused ion beam. FIGS. 32 and 33 are views schematically showing the positional relationship between the columnar portion 34 and the sample piece Q, FIG. 32 is based on the image obtained by the focused ion beam irradiation, and FIG. 33 is based on the image obtained by the electron beam irradiation. From FIGS. 32 and 33, the relative positional relationship between the columnar portion 34 and the sample piece Q is measured. As shown in FIG. 32, an orthogonal triaxial coordinate (a coordinate different from the triaxial coordinate of the stage 12) which has one corner of the columnar portion 34 as an original point 34a is determined, and distances DX and DY are obtained from FIG. 32 as a distance between the original point 34a of the columnar portion 34 and the reference point Qc of the sample piece Q.

Meanwhile, a distance DZ is obtained from FIG. 33. However, since the electron beam optical axis is inclined with respect to the focused ion beam axis (vertical) by an angle θ, the actual distance between the columnar portion 34 and the sample piece Q in the Z axis direction becomes DZ/sin θ.

Next, the movement stopping positional relationship of the sample piece Q with respect to the columnar portion 34 will be described with reference to FIGS. 32 and 33.

The positional relationship becomes a positional relationship in which the upper end surface 34b of the columnar portion 34 and the upper end surface Qb of the sample piece Q are the same surface as each other, the side surface of the columnar portion 34 and the cross section of the sample piece Q are the same surface as each other, and a gap of approximately 0.5 μm is provided between the columnar portion 34 and the sample piece Q. That is, the needle drive mechanism 19 is operated such that DX=0, DY=0.5 μm, and DZ=0 are satisfied, and the sample piece Q can reach at the target stop position.

Hereinafter, a tenth modification of the above-described embodiment will be described.

In Step 23 in the above-described embodiment, the needle 18 is operated by the needle drive mechanism 19 such that the gap between the columnar portion 34 and the sample piece Q measured from the image becomes the target value.

The processing from Step S22 to Step S25 in which the sample piece Q is connected to the sample piece holder P in the above-described embodiment may be performed as follows. That is, the attachment position of the sample piece Q with respect to the columnar portion 34 of the sample piece holder P is predetermined as the template, the image of the sample piece Q is pattern-matched to this position, and the needle drive mechanism 19 may be operated.

The template showing the movement stopping positional relationship of the sample piece Q with respect to the columnar portion 34 will be described. The positional relationship becomes a positional relationship in which the upper end surface 34b of the columnar portion 34 and the upper end surface Qb of the sample piece Q are the same surface as each other, the side surface of the columnar portion 34 and the cross section of the sample piece Q are the same surface as each other, and the gap of approximately 0.5 μm is provided between the columnar portion 34 and the sample piece Q. This template may be prepared by extracting the outline (edge) portion from the secondary particle image or the absorption current image data of the actual sample piece holder P and the needle 18 fixing the sample piece Q, and this template may be prepared from the design drawing as a line drawing.

The columnar portion 34 of the prepared template is displayed to overlap the image of the columnar portion 34 formed by the electron beam and the focused ion beam at real time, instruction of the operation is imposed to the needle drive mechanism 19, and the sample piece Q moves toward the stop position of the sample piece Q on the template (Steps 23 and 24). It is confirmed that the image formed by the electron beam and the focused ion beam at real time overlaps the predetermined stop position of the sample piece Q on the template, and processing of stopping the needle drive mechanism 19 is performed (Step 25). In this way, it is possible to correctly move the sample piece Q to the predetermined stopping positional relationship with respect to the columnar portion 34.

Next, another modification example of the above-described Steps 22 to 25 will be described.

In Step 23 of the above-described embodiment, the needle 18 is moved. If the sample piece Q which has been subjected to Step 23 is positioned at the positional relationship which deviates greatly from the target position, the following operation may be performed.

In Step 22, preferably, the position of the sample piece Q before the sample piece Q moves exists in a region in which Y>0 and Z>0 are satisfied in the rectangular triaxial coordinate system having the original point of each columnar portion 34. This is because collision between the sample piece Q and the columnar portion 34 hardly occurs during the movement of the needle 18. Accordingly, the X, Y, and Z drive portions of the needle drive mechanism 19 are simultaneously operated, and the sample piece Q can rapidly and securely reach the target position. Meanwhile, in a case where the sample piece Q is positioned in the region of Y<0 before the sample piece Q moves, if the X, Y, and Z drive portions of the needle drive mechanism 19 are simultaneously operated such that the sample piece Q is directed to the stop position, risk of collision between the sample piece Q and the columnar portion 34 increases. For this reason, in the case where the sample piece Q is positioned in the region of Y<0 in Step 22, the needle 18 reaches the target position through a path which avoids the columnar portion 34. Specifically, first, the sample piece Q moves to the region of Y>0 by driving only the Y axis of the needle drive mechanism 19 to reach the predetermined position, and next, the sample piece Q moves toward the final stop position by the simultaneous operations of the X, Y, and Z drive portions. According to this step, it is possible to securely and rapidly move the sample piece Q without collision with the columnar portion 34.

Moreover, in the above-described embodiment, the computer 21 may be a software function device, or may be a hardware function device such as LSI.

In addition, the above-described embodiment is exemplified, and does not limit the scope of the present invention. Various aspects may be applied to the new embodiments, and various omissions, replacements, and modifications may be applied within a scope which does not depart from the gist of the present invention. The embodiments and modifications are included in the scope or gist of the present invention, and are included in the inventions described in claims and the equivalent scope.

INDUSTRIAL APPLICABILITY

According to the present invention, since the computer 21 controls the beam irradiation optical systems 14 and 15, the drive mechanisms 13 and 19, and the gas supply portion 17 based on the templates of at least the sample piece holder P, the needle 18, and the sample piece Q which are acquired in advance, it is possible to provide the automatic sample preparation apparatus 10 capable of appropriately automating the operation of transferring the sample piece Q to the sample piece holder P.

BRIEF DESCRIPTION OF THE REFERENCE SYMBOLS

10: charged particle beam device, 11: sample chamber, 12: stage (sample stage), 13: drive mechanism, 14: focused ion beam irradiation optical system (charged particle beam irradiation optical system), 15: electron beam irradiation optical system (charged particle beam irradiation optical system), 16: detector (secondary particle detector), 17: gas supply portion, 18: needle, 19: needle drive mechanism, 20: display device, 21: computer, 22: input device, 33: sample bed, 34: columnar portion, P: sample piece holder, Q: sample piece, R: secondary charged particle, S: sample

The invention claimed is:

1. An automatic sample preparation apparatus which automatically prepares a sample piece from a sample, comprising:
a charged particle beam irradiation optical system configured to perform irradiation with a charged particle beam;
a sample stage configured to move with the sample placed thereon;
a sample piece transfer device for holding and transferring the sample piece separated and extracted from the sample;
a sample piece holder-fixing bed configure to hold a sample piece holder to which the sample piece is transferred;
a gas supply portion configured to irradiate gas forming a deposition film with the charged particle beam; and
a computer configured to control the charged particle beam irradiation optical system, the sample piece transfer device, and the gas supply portion to transfer the sample piece to the sample piece holder, based on at least an image which is previously acquired by the charged particle beam with respect to the sample piece held by the sample piece transfer device.

2. The automatic sample preparation apparatus according to claim 1,
wherein the computer is configured to extract an edge from the image of the sample piece holder acquired by the charged particle beam, and is configured to control a movement of the sample piece transfer device or the sample stage to transfer the sample piece to the sample piece holder, based on positional information which is obtained by template-matching using a template of the sample piece holder.

3. The automatic sample preparation apparatus according to claim 1,
wherein the charged particle beam is a focused ion beam, and
the charged particle beam irradiation optical system is a focused ion beam irradiation optical system, and
wherein the images are previously acquired from different directions by the focused ion beam with respect to the sample piece held by the sample piece transfer device.

4. The automatic sample preparation apparatus according to claim 1,
wherein the computer is configured to prepare at least the template of the sample piece held by the sample piece transfer device by extracting an edge from the image, and is configured to control a movement of the sample piece transfer device or the sample stage to transfer the sample piece to the sample piece holder based on positional information acquired by template-matching using the template.

5. The automatic sample preparation apparatus according to claim 1,
wherein the computer acquires the image at least in a state where a structure does not exist on a background of the sample piece held by the sample piece transfer device.

6. The automatic sample preparation apparatus according to claim 5,
wherein when the computer instructs the movement of the sample piece transfer device or the sample stage to be at least the state where a structure does not exist on the background of the sample piece held by the sample piece transfer device, in a case of not being the state where a structure does not actually exist on the background, the computer moves at least the sample piece connected to the sample piece transfer device to an initial position.

7. The automatic sample preparation apparatus according to claim 1,
wherein the computer acquires the image in a state where the sample piece transfer device rotates such that the sample piece has a predetermined posture.

8. The automatic sample preparation apparatus according to claim 4,
wherein the computer is configured to acquire the image again at least in a case where an edge cannot be extracted from the image with respect to a predetermined region of the sample piece held by the sample piece transfer device.

9. The automatic sample preparation apparatus according to claim 1,
wherein the computer acquires a distance between the sample piece held by the sample piece transfer device and the sample piece holder based on the image, and
wherein the computer controls the movement of the sample piece transfer device or the sample stage to transfer the sample piece to a predetermined position of the sample piece holder based on the distance.

10. The automatic sample preparation apparatus according to claim 1,
wherein the computer finally transfers the sample piece to a predetermined position of the sample piece holder by only a movement in a plane parallel to the sample stage.

11. The automatic sample preparation apparatus according to claim 4,
wherein the computer is configured to perform shape processing on the sample piece held by the sample piece transfer device before the template is prepared.

12. The automatic sample preparation apparatus according to claim 11,
wherein the computer is configured to set the position of the shape processing according to a distance from the sample piece transfer device.

13. The automatic sample preparation apparatus according to claim 1,
wherein the computer performs eccentricity correction when the sample piece transfer device holding the sample piece rotates to have a predetermined posture.

* * * * *